United States Patent
Chauhan et al.

(10) Patent No.: US 10,123,904 B2
(45) Date of Patent: Nov. 13, 2018

(54) PRESERVATIVE REMOVAL FROM EYE DROPS

(71) Applicant: University of Florida Research Foundation, Inc., Gainesville, FL (US)

(72) Inventors: Anuj Chauhan, Gainesville, FL (US); Kuan-Hui Hsu, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 15/502,876

(22) PCT Filed: Aug. 12, 2015

(86) PCT No.: PCT/US2015/044782
§ 371 (c)(1),
(2) Date: Feb. 9, 2017

(87) PCT Pub. No.: WO2016/025560
PCT Pub. Date: Feb. 18, 2016

(65) Prior Publication Data
US 2017/0224531 A1    Aug. 10, 2017

Related U.S. Application Data

(60) Provisional application No. 62/160,233, filed on May 12, 2015, provisional application No. 62/036,670, filed on Aug. 13, 2014.

(51) Int. Cl.
*A61F 9/008* (2006.01)
*A61K 31/5377* (2006.01)
(Continued)

(52) U.S. Cl.
CPC ........... *A61F 9/0008* (2013.01); *A61J 1/1456* (2015.05); *A61K 9/0048* (2013.01);
(Continued)

(58) Field of Classification Search
CPC .. A61F 9/0008; A61J 1/1456; A61K 31/5377; A61K 31/38
See application file for complete search history.

(56) References Cited

U.S. PATENT DOCUMENTS 5,056,689 A     10/1991   Heyl et al.
5,080,800 A *    1/1992   Heyl ..................... A61F 9/0008
                                                         210/679
(Continued)

OTHER PUBLICATIONS

"Bio-Rex Weakly AcidicCation Exchange Resin Instruction Manual". Bio-Rad. Jan. 14. 2014 <http://www.bio-rad.com/webroot/web/pdf/lsr/literature/LIT206.pdf>.*
(Continued)

*Primary Examiner* — Tatyana Zalukaeva
*Assistant Examiner* — Sara Sass
(74) *Attorney, Agent, or Firm* — Marshall, Gerstein & Borun LLP

(57) ABSTRACT

A BAK removal device is constructed as a plug of microparticles of a hydrophilic polymeric gel that displays a hydraulic permeability greater than 0.01 Da. The polymer hydrophilic polymeric gel comprises poly(2-hydroxyethyl methacrylate) (pHEMA). The particles are 2 to 100 μm and the plug has a surface area of 30 mm² to 2 mm² and a length of 2 mm to 25 mm and wherein the microparticles of a hydrophilic polymeric gel has a pore radius of 3 to 60 μm.

21 Claims, 18 Drawing Sheets

(51) Int. Cl.
*A61K 31/382* (2006.01)
*A61F 9/00* (2006.01)
*A61J 1/14* (2006.01)
*A61K 31/5575* (2006.01)
*A61K 31/573* (2006.01)
*A61K 47/18* (2017.01)
*A61K 9/00* (2006.01)
*C08J 9/28* (2006.01)
*B01D 15/00* (2006.01)
*B01J 20/26* (2006.01)

(52) U.S. Cl.
CPC ........ *A61K 31/382* (2013.01); *A61K 31/5377* (2013.01); *A61K 31/5575* (2013.01); *A61K 31/573* (2013.01); *A61K 47/186* (2013.01); *B01D 15/00* (2013.01); *B01J 20/261* (2013.01); *C08J 9/286* (2013.01); *C08J 2205/022* (2013.01); *C08J 2205/044* (2013.01); *C08J 2207/10* (2013.01); *C08J 2333/14* (2013.01)

(56) References Cited

U.S. PATENT DOCUMENTS

| | | | | |
|---|---|---|---|---|
| 5,496,471 | A | * | 3/1996 | Heyl ............... A61F 9/0008 210/266 |
| 5,588,559 | A | | 12/1996 | Vallet Mas et al. |
| 5,681,463 | A | * | 10/1997 | Shimizu ............ B01D 61/18 210/266 |
| 5,936,061 | A | | 8/1999 | Andersson et al. |
| 6,669,848 | B2 | | 12/2003 | Kuhn |
| 2004/0058056 | A1 | * | 3/2004 | Osaki ............... A61L 29/06 427/2.1 |
| 2006/0093999 | A1 | * | 5/2006 | Hei ................... A61L 2/00 435/2 |
| 2010/0098761 | A1 | * | 4/2010 | Song ............. A61K 38/1866 424/486 |
| 2010/0238447 | A1 | | 9/2010 | Hirsch | |

OTHER PUBLICATIONS

Baudouin, C. et al., "Short term comparative study of topical 2% carteolol with and without benzalkonium chloride in healthy volunteers," *British Journal of Ophthalmology*, 1998, pp. 39-42, vol. 82.

Baudouin, C. et al., Preservatives in eyedrops: The good, the bad, and the ugly, *Progress in Retinal and Eye Research*, 2010, pp. 312-334, vol. 29.

Ishibashi, T. et al., "Comparison of the Short-Term Effects on the Human Corneal Surface of Topical Timolol Maleate With and Without Benzalkonium Chloride," *Journal of Glaucoma*, Dec. 2003, pp. 486-490, vol. 12, No. 6.

Jaenen, N. et al., "Ocular symptoms and signs with preserved and preservative-free glaucoma medicaitons," *European Journal of Ophthalmology*, 2007, pp. 341-349, vol. 17, No. 3.

Kim, J. et al., "Dexamethasone transport and ocular delivery from poly(hydroxyethyl methacrylate) gels," *International Journal of Pharmaceutics*, 2008, pp. 205-222, vol. 353.

Malet, F. et al., "Preservative-Free Ocular Hydrating Agents in Symptomatic Contact Lens Wearers: Saline versus PVP Solution," *Eye & Contact Lens*, 2003, pp. 38-43, vol. 29, No. 1.

Nuzzi, R. et al., "Conjuctiva and subconjunctival tissue in primary open-angle glaucoma after long-term topical treatment: an immunohistochemical and ultrastructural study," *Graefe's Arch Clin Exp Ophthalmol*, pp. 154-162, vol. 233.

Rolando, M. et al., "The Effect of Different Benzalkonium Chloride Concentrations on Human Normal Ocular Surface," *The Lacrimal System*, 1991, pp. 87-91, Kugler and Ghedina Publications.

Teping, C. et al., "The COMOD system. A preservative-free multidose container for eyedrops," *Klin Monatsbl Augenheilkd*, 1994, pp. 210-217, vol. 205.

* cited by examiner

PRESERVATIVE REMOVAL FROM EYE DROPS

CROSS-REFERENCE TO A RELATED APPLICATIONS

This application is the U.S. national stage application of International patent application No. PCT/US2015/044782, filed Aug. 12, 2015, which claims the benefit of U.S. Provisional Application Ser. No. 62/160,233, filed May 12, 2015 and U.S. Provisional Application Ser. No. 62/036,670, filed Aug. 13, 2014, the disclosures of which are hereby incorporated by reference in their entireties, including all figures, tables and drawings.

BACKGROUND OF INVENTION

Ophthalmic diseases are most commonly treated by instillation of eye drops with frequencies varying from one or two a day for diseases like glaucoma to as many as ten a day for severe infections. The drug solutions in eye drop bottles can get contaminated during use due to contact of the tip with hands or tears while instilling the drops. In a recent study with 204 glaucoma patients, only 39% were able to instill the eye drops without touching the bottle to the eye surface. There are additional risks of cross-contamination when multiple patients share a bottle, such as in a family or in hospitals. The high potential for the contamination after opening the bottles has led to regulations that require the addition of an antimicrobial agent in multi-dose eye drop formulations. Several preservatives have been researched and used in commercial formulations, including: alcohols, parabens, EDTA, chlorhexidine, and quaternary ammonium compounds. In addition to antimicrobial efficacy, the preservatives require suitable physical properties for incorporation into the formulations, such as chemical and thermal stability, compatibility with the eye drop container and other compounds in the formulation, and, more importantly, negligible toxicity to ocular tissues.

Regulations require that ophthalmic preservatives achieve 1.0 and 3.0 log reduction by days 7 and 14, respectively, along with no increase in survivors from days 14-28 and no increase in survivors for the fungi from day 0 to day 28 after inoculation with $10^6$ colony forming units (cfu)/mL. (Baudouin et al. "Preservatives in Eyedrops: the Good, the Bad and the Ugly". Progress in Retinal and Eye Research, 2010, 29, 312-34) Due to high efficacy and low corneal toxicity, the quaternary ammonium compounds are preferred preservatives. Benzalkonium chloride:

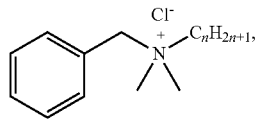

where a mixture of n being 8, 10, 12, 14, 16, and 18, is the most common choice with n=12 and 14 being the primary homologues. Eye drop formulations require BAK at concentrations ranging from 0.004 to 0.025% (w/w) to achieve the regulatory effectiveness. In spite of the positive safety profile of BAK, achievement of the targeted antimicrobial and antifungal effects is not possible without levels that cause some toxic side effects to the cornea. BAK can cause tear film instability, loss of goblet cells, conjunctival squamous metaplasia and apoptosis, disruption of the corneal epithelium barrier, and damage to deeper ocular tissues.

The potential for ocular damage from the preservatives is particularly high among patients suffering from chronic diseases that require daily eye drop instillations for periods of years to decades, such as glaucoma patients. Several clinical and experimental studies have shown that toxic side effects from preservative free eye drops are significantly lower than from their preserved counterparts. A multicenter cross-sectional epidemiologic study using preservative or preservative-free beta-blocking eye drops showed that patients on preservative free eye drops exhibit significantly fewer ocular symptoms and signs of irritation compared to those using preserved eye drops. (Jaenen et al. "Ocular Symptoms and Signs with Preserved and Preservative-free Glaucoma Medications", European Journal of Ophthalmology. 2007, 17, 341-9) Preserved glaucoma drug timolol causes significantly higher tear film instability and disruption of corneal barrier function than preservative-free timolol in healthy subjects. (Ishibashi et al., "Comparison of the Short-term Effects on the Human Corneal Surface of Topical Timolol Maleate with and without Benzalkonium Chloride", Journal of Glaucoma, 2003, 12, 486-90) Similar results were found when comparing preservative-free and BAK-containing carteolol. (Baudouin et al., "Short Term Comparative Study of Topical 2% Carteolol with and without Benzalkonium Chloride in Healthy Volunteers", British Journal of Ophthalmology. 1998, 82, 39-42) Goblet cell loss and increased cytoplasmic/nucleus ratio, two characteristics of dry eye disease, have been shown to occur when using BAK containing tear substitutes. (Rolando et al., "The Effect of Different Benzalkonium Chloride Concentrations on Human Normal Ocular Surface". The Lacrimal System, Kugler and Ghedini, New York 1991, 87-91) A significant reduction in Schirmer test values was observed for subjects receiving BAK eye drops compared with subjects not receiving therapy. (Nuzzi et al., "Conjunctiva and Subconjunctival Tissue in Primary Open-angle Glaucoma after Long-term Topical Treatment: an Immunohistochemical and Ultrastructural Study", Graefe's Archive for Clinical and Experimental Ophthalmology, 1995, 233, 154-62) Patients using preserved eye drops and experiencing toxicity symptoms, such as allergy, blepharitis or dry eye, experienced rapid improvements upon switching to preservative-free formulations. Such studies suggest a role of preservatives in the preponderance of dry eye symptoms in glaucoma patients, who typically use multiple drugs with multiple instillations each day.

BAK is considered a 'necessary evil' for prevention of microorganism growth in the bottles while displaying toxic effects on the ocular tissue. The industry has taken a few approaches to solve this problem. One approach is to develop more efficacious glaucoma therapies, such as: use of prostaglandins that require instillation of only one eye drop each day; and combinations that contain multiple drugs in the same formulation to eliminate instillation of multiple eye drops. Nevertheless, both of these approaches still permit a cumulative effect to preservatives over long periods of time. Furthermore, only a few combination products are available, generally combinations from a single manufacturer.

A second approach is to provide single dose packages, and several glaucoma formulations are now available as preservative free single doses. While this approach can eliminate exposure to preservatives, in addition to increasing manufacturing costs and the environmental impact of packaging, single dose formulations contain about 0.3 to 0.4 mL of formula, which is significantly more than the typical eye drop volume of 30 Lµ, leading to wastage or possibly misuse of the same package for multiple days. This approach can suffer if bacterial contamination occurs prior to packaging.

Another approach is to replace BAK with a less toxic preservative, such as: Purite®, a stabilized oxychloro complex; and Sofzia®, which is composed of boric acid, propylene glycol, sorbitol, zinc chloride and polyquaternium compounds, some of which are used in contact lens care solutions. While these alternatives may be promising, no data on long term impact from use of these preservatives is available, and consistent use of these preservatives over extended periods of years may well prove them toxic.

The solution in a bottle is typically contaminated during the instillation of the eye drops due to the contact of the bottle tip with the eye surface, contact of the tip with hands, or both. As the eye drop detaches from the bottle, a small volume of liquid remaining at the tip is sucked back, which can take the bacteria into the bottle, leading to the contamination. An ABAK® (Laboratoires Théa, France) design introduces a 0.2 µm filter at the top of the bottle to filter out bacteria from the re-entering solution, thereby preventing contamination. Though effective, this approach does not protect against contamination prior to packaging. Also the 0.2 µm filter could require additional pressure to push the drops, making drop instillation difficult, particularly for the elderly. Additionally, any leak in the filter or bacteria transport through the pores could allow the formulation in the bottle to get contaminated. It is also not clear whether this design can protect against growth of bacteria trapped in the filter. The COMOD® (Ursapharm, Germany) system combines an air free pump and an inner lining that retracts as the liquid is pushed out to avoid contamination of the contents of the bottle. While this design is innovative and useful, its complexity and increased cost are major concerns. As with ABAK®, COMOD® cannot protect against any microorganisms introduced due to errors in the manufacturing processes causing loss of sterility. This makes the filling of these devices complicated because sterility is essential at each step.

U.S. Pat. No. 5,080,800 teaches a process for removing components from solutions, including preservatives from eye-drops. The process involves the use of ion exchange resins to selectively remove ocular preservatives. Ion exchange resins have not been tested extensively for biocompatibility and cytotoxicity and inherently are non-selective, adsorb ionic drugs as readily as any ionic preservative such as BAK. The hydraulic permeability of these resins is not addressed although this characteristic is critical for devices that allow formation of drops without excessive pressure. U.S. Pat. No. 5,080,800 also does not teach on the importance of ensuring that the filters are designed to resist growth of microorganisms that may remain trapped. U.S. Pat. No. 5,080,800 does not teach on the possibility of dilution of the BAK concentration in the formulation because of draining of the BAK free formulation from the filter into bottle after each eye drop instillation. Hence a practical way of retaining the beneficial behavior of preservatives while avoiding their toxic effects in the eye remains a need.

BRIEF SUMMARY

Embodiments of the invention are directed to a preservative removing device having a plug of microparticles that are a hydrophilic polymeric gel. The plug has a shape that matches an outlet to a container for a solution, emulsion, or suspension. The hydrophilic polymeric gel swells in the presence of the solution, emulsion, or suspension and selectively absorbs a preservative contained therein. The plug of microparticles has a hydraulic permeability greater than 0.01 Da, even greater than 10 Da in some embodiments. The hydrophilic polymeric gel can be poly hydroxyl ethyl methacrylate (pHEMA) or a pHEMA copolymer such as poly hydroxyl ethyl methacrylate-co-methacrylic acid, or other biocomptabile polymer, including but not limited to, dimethyl acrylamide, methyl methacrylate, and silicones. The hydrophilic polymeric gel has interconnected pores, wherein the pores have an average radius of 1 to 60 The microparticles can be from 2 to 100 µm in cross-section. The preservative removing device can remove the preservative benzalkonium chloride (BAK).

In an embodiment of the invention, the hydrophilic polymeric gel is a preservative containing device, for example, a gel that is preloaded with the BAK at a concentration of one to 100 times that of the solution, emulsion, or suspension in the container. The preservative incorporation into the device would impart sterility, which is a requirement for all ophthalmic preparations and dispensers. The preservative incorporated device could also act as a preservative removal device if the initial loading is below the equilibrium capacity. Additionally, the plug can include antibacterial microparticles, such as, silver particles.

In an embodiment of the invention, the polymeric material can be pretreated with a drug in the solution, emulsion, or suspension in the container, wherein the polymer is less than saturated or saturated with the drug to reduce or eliminate further drug uptake during the dispensing of the solution, emulsion, or suspension.

In an embodiment of the invention the preservative removing device is included in a multi-dosing device for delivery of an ophthalmic solution is a compressible bottle that has an outlet extension containing the preservative removing device. When the hydrophilic polymeric gel is dry, it has dimensions smaller than the internal dimensions of the outlet extension but has larger than the internal dimensions of the outlet extension when swollen with the ophthalmic solution. The multi-dosing device can include an ophthalmic agent selected from timolol, dorzolamide, dexamethasone phosphate, dexamethasone, latanoprost or other prostaglandins, rewetting eye drops, or any other compounds that is delivered to the eye for disease treatment or comfort improvement.

In another embodiment of the invention, a method of administering an ophthalmic agent involves providing a compressible bottle with a preservative removing device at the outlet of the compressible bottle containing an ophthalmic agent and a preservative, which upon applying pressure to the compressible bottle; the solution is forced through the preservative removing device.

In another embodiment of the invention, a method of administering an ophthalmic agent involves providing a compressible bottle with a preservative removing device at the outlet of the compressible bottle containing an ophthalmic agent and a preservative, and a preservative loaded film at the bottom of the bottle which upon applying pressure to the compressible bottle; the solution is forced through the preservative removing device.

BAK mixture solution through 1.8 cm thick plug of pHEMA particles prepared by using SR454HP as cross-linker packed in the tip of the eye drop prototype for 10 daily runs over 10 days where the data points are mean±SD with n=3.

Figure 27:
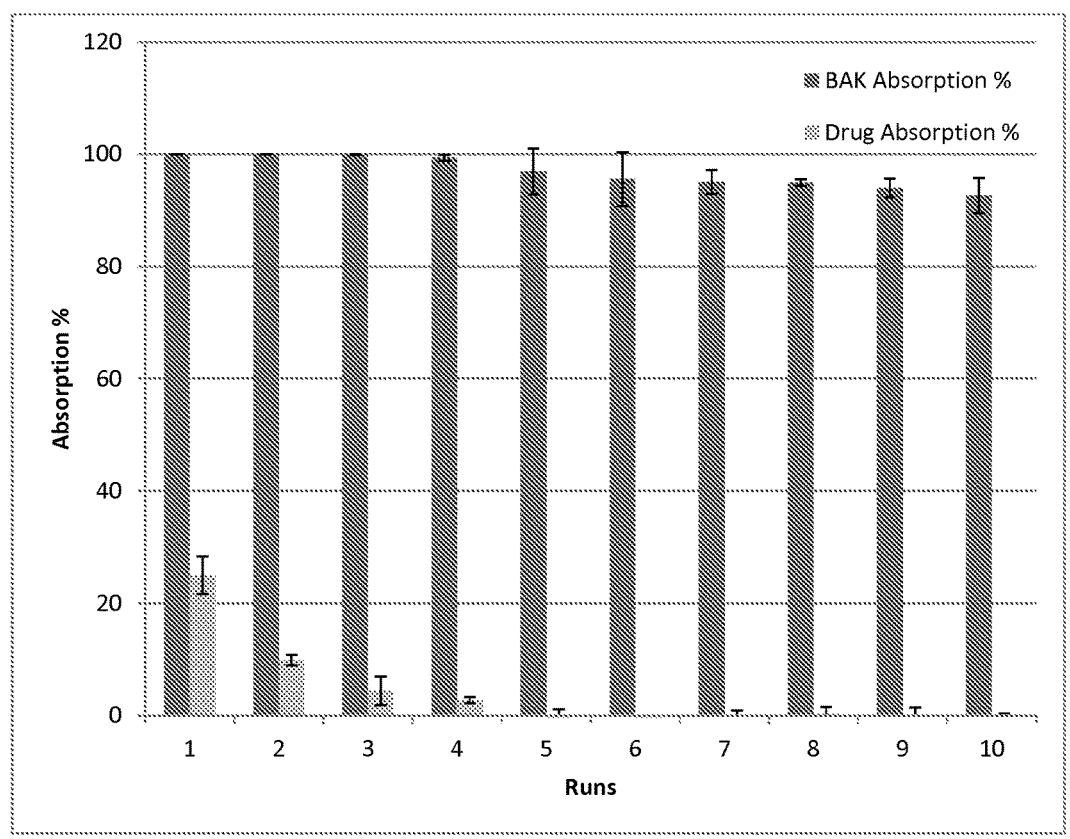

FIG. 27 shows a bar chart of the percentages of BAK and timolol that are removed after passing 1.5 mL of a timolol/BAK mixture solution through 1.8 cm thick plug of pHEMA particles prepared by using SR9035 as cross-linker packed in the tip of the eye drop prototype for 10 daily runs over 10 days where the data points are mean±SD with n=3.

DETAILED DISCLOSURE

Figure 1A:
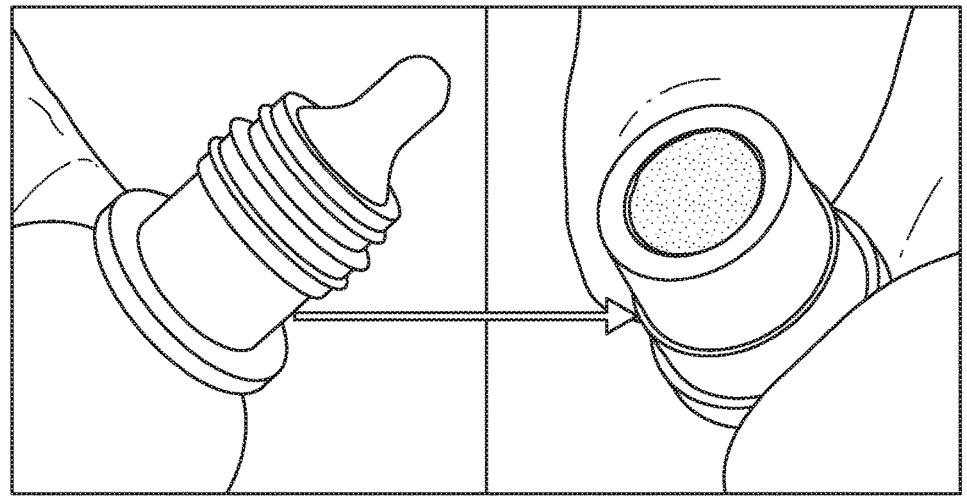
FIG. 1A shows a photograph of a prototype design with a filter, according to an embodiment of the invention, incorporated into the neck of the eye drop bottle
Figure 1B:
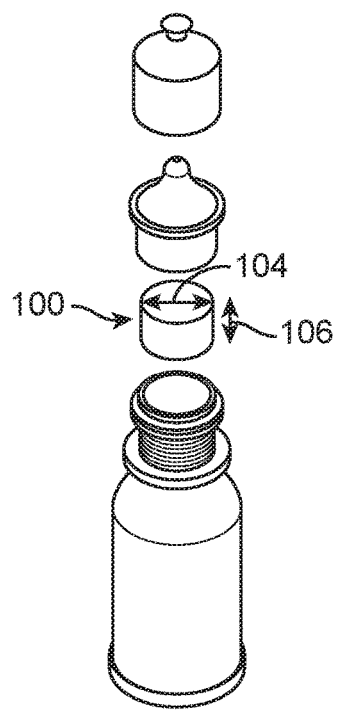
FIG. 1B shows a CAD design of a bottle, filter, tip and cap assembly of the device.
Figure 2A:
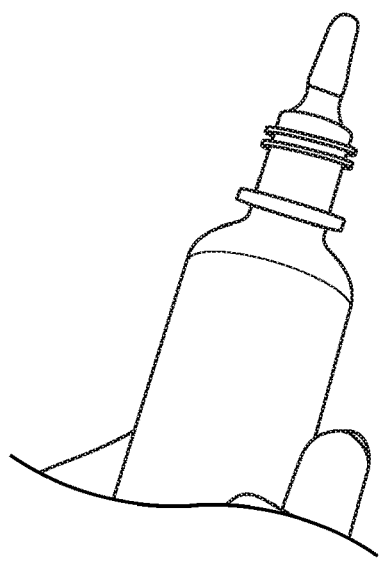
FIG. 2A shows a photograph of a prototype design with the filter incorporated into the tip of the eye drop bottle and FIG. 2B shows a CAD design of a bottle, filter, tip, and cap assembly of the device
Figure 2B:
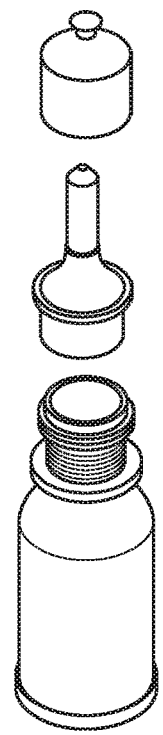

Embodiments of the invention are directed to a multi-dosing device and method that eliminates patients' exposure to preservatives, particularly BAK, in delivered eye drops while retaining BAK in the contained formulation and ensuring that the eye drop bottle remains sterile. Benefit of the BAK for storage is retained while the potential for ocular toxicity from BAK is eliminated. In an embodiment of the invention, a porous preservative removing device, also referred to herein as a plug, is situated in the neck of the eye drop bottle leading to the drop exit, as shown in FIG. 1. In another embodiment of the invention, the plug is situated in a section of the tip of the eye drop bottle, as shown in FIG. 2. A large tip is included in the bottle to allow a long plug to be positioned therein The preservative removing device can be separate filter that is attached to the formulation dispensing unit through a suitable connector for use. The plug must display a high hydraulic permeability such that relatively little pressure is required to dispense a fluid. The needed hydraulic permeability depends on the design of the filter, where larger pores allow higher liquid flow for a given pressure drop. In embodiments of the invention, hydraulic permeability is larger than about 0.01 Da and a permeability of about 0.1 Da is adequate for the typical embodiment of the invention where the plug is one that fits a size that fits state of the art eye drop packages. A hydraulic permeability of 1 to 10 Da can ensure that the fluid that remains in the filter after instillation of the eye drop is sucked back into the bottle. A larger hydraulic permeability allows the same plug to work for a wide range of formulations including high viscosity formulations, such as, rewetting eye drops.

In an embodiment of the invention the preservative removing device is included in a multi-dosing device for delivery of an ophthalmic solution is a compressible bottle that has an outlet extension containing the preservative removing device. When the hydrophilic polymeric gel 100 is dry, it has dimensions 104, 106 smaller than the internal dimensions of the outlet extension but has dimension 104, 106 larger than the internal dimensions of the outlet extension when swollen with the ophthalmic solution. The multi-dosing device can include an ophthalmic agent selected from timolol, dorzolamide, dexamethasone phosphate, dexamethasone, latanoprost or other prostaglandins, rewetting eye drops, or any other compounds that is delivered to the eye for disease treatment or comfort improvement.

The plug is of a material with high affinity for the preservative BAK and low affinity for the drug or other opthalmological agent, such that at least 50 percent of the preservative is removed from the solution by the plug and at least 50 percent of the drug is retained by the solution that is dispensed from the device. The high affinity is a necessary but not a sufficient requirement because the concentration in the eluting liquid may not be in equilibrium with that in the plug due to the short contact time of 1-3 sec. In addition to the high partition coefficient, the adsorption rate constant must be sufficiently high so that the time for adsorption of a drug molecule to the polymer is less than the contact time of 1-3 sec. Furthermore it is also important that the pore size in the plug is small enough so that the molecules that are initially far away from the surface of the polymer in the plug can diffuse towards the polymer and adsorb. When the plug material has a high partition coefficient and adsorption rate and the pore size in the plug is optimized, all or most of the preservative will adsorbs on the pore surfaces in the plug and the eluting drops will be preservative-free. The preservative free liquid that elutes through the plug is instilled directly into the eyes. The highly porous plug material selectively extracts the preservative, allowing the eye drop formulation to flow through the plug with only a small pressure drop, yet allowing sufficient time and surface area to bind the preservative.

The material selected is critical, allowing for construction of a safe, biocompatible filter for preservative removal. Previous patents have proposed ion exchange resins for similar applications but such materials may also remove ionic drugs. For example, BAK is cationic and a number of ophthalmic drugs such as timolol are cationic at physiological pH and thus the ion exchange resins may remove both. A number of materials have been widely used for ophthalmic applications and such materials are compatible with the eye. Poly(2-hydroxyethyl methacrylate) (pHEMA) is one of the most commonly used material for devices used in the eye, but has never been explored for its use as a permeable liquid plug for removal of any ionic materials. Since pHEMA in non-ionic, high binding of BAK or other ionic compounds is not possible in the manner of an ion exchange material. We started with pHEMA due to its excellent biocompatibility and assumed that we would need to incorporate other components into the material to obtain the desired selectivity for BAK. Surprisingly, it was observed that pHEMA is extremely effective in adsorbing BAK without any modifications. The pHEMA material has a high partition coefficient for BAK and the adsorption times were determined to be less than the transit time of 3 s, implying that BAK solution flowing through a pHEMA plug will have sufficient time to adsorb on the polymer. Furthermore, pHEMA is already used as an ophthalmic material, making it the ideal choice for the plug material.

In an embodiment of the invention, the plug material is a hydrogel, such as poly(2-hydroxyethyl methacrylate) (pHEMA). The pHEMA hydrogel displays an extremely high binding capacity for BAK with a partition coefficient of about 100-500 depending on the BAK concentration and the structure of the pHEMA matrix used in the measurement. In contrast, the partition coefficients of most hydrophilic ophthalmic drugs into the pHEMA matrix range from about 1 to 10, and partition coefficients of hydrophobic drugs are in the range of 10 to 50. When a drug's partition coefficient into the plug is lower by at least an order of magnitude than the plugs affinity for BAK, the porous pHEMA plug permits selective removal of BAK from eye drop formulations.

In an embodiment of the invention, the pHEMA plug is highly porous, having large interconnected pores that allow easy solution flow with the preservative BAK adsorbing on the walls of the pores. The plug can be formed as a porous gel, a packed bed, or a structure formed by 3D printing, soft lithography, electrospinning, or any other method. Use of a macroporous gel, according to an embodiment of the invention, permits a relatively simple scalable preparation process that is cost effective. Macroporous gels are biphasic materials consisting of large interconnected pores dispersed throughout the polymer. The macroporous hydrogels can be prepared by free radical polymerization of a monomer in a diluent that dissolves the monomer but not the polymer. If the concentration of the diluent is more than the equilibrium swelling capacity of the polymer, the extra diluent phase separates and forms pores. Although macroporous pHEMA hydrogels can be prepared using water as the diluent, such gels are typically weak mechanically. Organic diluents with good solubility for HEMA but poor solubility for pHEMA include dodecan-1-ol and 1, 2-dichloroethane, and such solvents result in robust gels. However, significant amount of organic liquids is undesirable for biomedical applications. Therefore, the macroporous hydrogels are prepared by enhanced phase separation using aqueous NaCl solution. In another embodiment of the invention, the macroporous gel could be prepared from other suitable polymers such as poly acrylamide and pHEMA particles could be dispersed as the matrix for sequestration of the preservative.

Alternatively, in an embodiment of the invention, the plug can be prepared as a packed bed of pHEMA or other polymeric particles. The particles can be macroporous. The packed beds of macroporous particles can have three levels of porosity: the space between the spherical particles providing inter-connected channels for the liquid flow; the macropores in the spherical particles to allow BAK diffusion into the particles and adsorb on the surface of these pores; and the pHEMA polymer's inherent porosity having nano-sized pores which provide the surface area for high BAK uptake into the gel. In a packed bed, the multiple levels of porosity avoids any tradeoff between increased permeability and reduced area, and, thus, increasing the particle size to increase the hydraulic permeability with minimal impact on the surface area for adsorption of BAK. Non spherical particles could be very useful as well in achieving high porosity that will increase the hydraulic permeability.

Nano or micron sized polymeric particles (nanogels or microgels) are produced by solution or bulk polymerization, where bulk gelation is avoided by using dilute monomer solutions or by using chain transfer agents and restricting the conversion of monomer to polymer. For example, the water fraction is significantly high to prevent macroscopic gelation of the microgels. By varying the water fraction, and other formulation parameters, particles ranging from 5 to 50 μm in size can be produced. We observed that the type of the cross-linker has a very significant impact on the type and size of particles produced. Additionally or alternatively, a chain transfer agent can be used to effectively cap the growing chains on the surfaces of microparticles. By manipulating the degree of dilution, salt concentration, and the concentration of chain transfer agent, a wide particle size range can be produced. The particles will be dried and then packed in a bed to create the monolith for BAK separation.

In another embodiment of the invention, cryogels are prepared by freezing a polymerization mixture and using a redox couple as the initiator to polymerize under frozen conditions. Cryogels typically have large pores in the range of tens to hundreds of microns. The initiator can be a mixture of N,N,N',N'-tetramethylethylene diamine (TEMED) and ammonium persulfate (APS). The mixture is frozen at −15° C. for 12 hours and then thawed.

In embodiments of the invention, various filters may be placed to support the porous matrix or the particles. The filter is designed to offer minimum resistance to fluid flow.

Other embodiments of the invention are directed to a method of incorporating the preservatives into particles that are added to the formulation in the containers such that the particle-incorporated preservative can provide the required preservative effect, but not flow out with the formulation. The particles can directly impart the preservative effect such as colloidal silver particles. The particles in the formulation are prevented from eluting, either by attachment to the container walls through long polymeric chains, or by placing a filter at the exit from the device of size smaller than the particles. In another embodiment of the invention, the walls of the container or other surfaces can have attached or incorporated preservative, to provide the preservative effect to the formulation. For example, the preservative source can be a pHEMA membrane with 1-10% by volume of the initial formulation volume, equilibrated with BAK at the starting concentration in the formulation. In another embodiment of the invention, the entire container can be a porous material with the formulation contained in the pores and the preservative incorporated into the polymer providing the preservative effect.

In another embodiment of the invention, the surface of the device from which the drops ultimately elute and the surface of the pores in the plug or the spherical particles in the plug can incorporate additional preservative, either through adsorption or by attachment or otherwise be incorporated as particles to ensure that any liquid left in the pores does not promote growth of microorganisms. As an example, the plug can be pre-loaded with BAK at a suitable concentration to ensure that any microorganism that is trapped in the plug does not grow over time. In another embodiment, other antimicrobial particles, such as, silver particles, can be incorporated into the plug to achieve the preservative action.

Typical eye drop dispensing systems employ a similar basic design. A plastic bottle is elastic such that the application of force by the fingers pressing on the bottle leads to deformation that compresses the air in the bottle to impose an increase in pressure on the liquid, which leads to drop creation at the tip. The flow of liquid out of the bottle results in an increase of the gas phase volume and a decrease in pressure. The pressure needed for the drop creation must exceed the Young Laplace pressure during drop creation, which is about $2\sigma/R_d$ where $\sigma$ is the surface tension and $R_d$ is the radius of the drop. Estimating $R_d$~0.5 mm based on a drop volume of 30 μL, and using surface tension of water for $\sigma$, gives a value of about 100 Pa for the Young Laplace pressure. Assuming an ideal gas law, to achieve this pressure, the volume of the gas phase ($\Delta P$) in the bottle must decrease by the volume $\Delta V=\Delta P/P*V$, where P is the starting pressure in the bottle (1 atmosphere) and V is the volume of the air phase. Substituting approximate values of all parameters gives $\Delta V/V=0.1\%$, which means that the pressure applied by the hands must be sufficient to achieve a 0.1% decrease in the volume of the bottle. However, an additional $\Delta V$ equaling the volume of the drop is required to compensate for the increase in the volume of the gas phase due to the volume of liquid pushed out of the bottle. The volume of typical eye drops is about 30 μL, which is larger than the 0.1% of the volume of the bottle. Thus, the volume reduction necessary for dispensing the eye drop is approximately equal to the volume of the drop itself. The pressure generated in the gas phase from this compression, estimated by the ideal gas law, where $\Delta V=30$ μL, $V=3$ mL, $P=1$ atm, indicates a minimum JP of about 0.01 atm=1000 Pa. This represents the minimum pressure needed to create the drop. Most subjects can easily apply 5-10 times this pressure.

Drop dispensing is more complex in a plug containing device, according to an embodiment of the invention, due to the extra pressure required to push the fluid through the plug As a patient squeezes the bottle, the increased pressure in the gas phase will push liquid through the plug. Initially, the entire pressure drop will occur across the plug because the drop has not yet formed. As the drop forms and its volume increases, the Young Laplace pressure increases, reducing the available pressure drop for flow through the plug. The rate of liquid flow through the plug depends on the applied pressure as well as the design parameters including the length, area, porosity, and hydraulic permeability. These parameters are required of a plug such that a subject can instill the eye drop from the bottle containing the plug without having to apply excessive pressure while the plug removes the desired amount of the preservative from each eye drop till the entire formulation is used. It is not a trivial exercise to determine a desired pore size and hydraulic permeability. A higher pore size and permeability facilitates instillation of the eye drops but reduces the time of transit through the plug and the available surface area, which reduces the mass of preservative removed. Other aspects of the plug performance depend on the hydraulic permeability. For example, after the eye drop is instilled, the subject stops squeezing the bottle. This creates a vacuum inside the bottle, which retracts the remaining fluid at the tip of the bottle. When the bottle contains the plug, the entire plug is full of the fluid after the eye drop is instilled. The vacuum inside the eye drop bottle could such back the entire fluid from the plug but that would depend on the hydraulic permeability as well as the surface tension and the contact angle of the formulation with the plug material. If the hydraulic permeability is not sufficiently large, the plug retains the formulation between two successive instillations. This is beneficial to the instillation process, as the volume of fluid needed to be transferred would simply be the drop volume. However, the tip must be properly sealed to minimize evaporation from the fluid filled plug. It is critical to ensure that the plug displays pores of the plug that is a sterile environment as the preservative from the formulations would be taken up by the plug. Even with a very high hydraulic permeability, some fluid is potentially trapped, necessitating the plug designed to maintain sterility, for example, by preloading the plug with BAK, or an antimicrobial coating, or by adding antimicrobial particles in the plug. With each drop instillation, the concentration of BAK in the plug increases, thereby assuring the sterility of the plug.

Below is provided a mathematical model of the fluid flow through the plug and the BAK uptake that permits determination of physical properties displayed by a plug (pore size, hydraulic permeability, cross sectional area, length) that allow one to achieve the objectives of eye drop instillation without a significant increase in the pressure required and permit BAK removal to the desired extend from the entire formulation. It should be understood that the model is for a simplified version of the device, yet permits estimates on the design parameters to achieve the desired separation. Experiments would eventually be needed to optimize the device starting from the parameters suggested by the model.

The pressure drop through the plug can be estimated by Darcy's Law:

$$q = \frac{k}{\mu}\frac{\Delta P}{H}A \qquad [1]$$

where k is the hydraulic permeability of the material, L is the length, $\mu$ is fluid viscosity, $\Delta P$ is the pressure drop across the plug and A is the cross-sectional area. The average flow rate through the plug is the ratio of the volume of the drop $V_d$ (=30 µL) and the time needed to form the drop $\tau$. We want $\tau$ of about 3 s, which is comparable to the time taken to form a drop with most commercial bottles. Consideration of the drop forming mechanics leads to the following constraint:

$$\frac{V_d}{\tau} = \frac{k}{\mu}\frac{\Delta P}{H}A \qquad [2]$$

Plugs, according to an embodiment of the invention, are designed to selectively remove nearly all preservative BAK without reducing the concentration of the active pharmaceutical ingredient (API). The plug must have sufficient capacity for absorbing the preservatives loaded in the bottle where the interactions between the plug material and the preservative must be sufficiently strong to eliminate any desorption. The kinetics of preservative uptake by the material of the plug is very rapid, such that the time scale for binding is shorter than the time scale for flow of the formulation through the plug.

The macroporous gel can be modeled as a set of parallel pores of length L and radius R to address the fluid flow and mass transfer in the macroporous gel and determine a structure that can achieve separation goal of removing >90% BAK with a fluid flow where no increase in the pressure is required to create the drops. The concentration in pore c(r, z, t) is a function of the radial position in the pore r, axial position along the plug z, and time t. The solution of the convection-diffusion equation for BAK transport in the pore requires establishing appropriate initial and boundary conditions $$\frac{\partial c}{\partial t} + u(z)\frac{\partial c}{\partial z} = D\left[\frac{\partial^2 c}{\partial z^2} + \frac{1}{r}\frac{\partial}{\partial r}\left(r\frac{\partial C}{\partial r}\right)\right] \qquad [3]$$

where the velocity through the pore is given by the Poiseuille flow profile, i.e., $$u(z) = 2\langle u\rangle\left[1-\left(\frac{r}{R}\right)^2\right] \qquad [4]$$

where <u> is the average velocity of the fluid through the gel. To solve the above convection-diffusion equation, the boundary and initial conditions are:

$$c(r, z=0, t) = c_0 + \frac{D}{\langle u\rangle}\frac{\partial c}{\partial z}(r, z=0, t) \qquad [5]$$

$$\frac{\partial c}{\partial z} = (r, z=L, t) = 0 \qquad [6]$$

$$c(r=R, z, t) = 0 \qquad [7]$$

$$\frac{\partial c}{\partial r}(r=0, z, t) = 0 \qquad [8]$$

$$c(r, z, t=0) = 0 \qquad [9]$$

where $c_0$ is the inlet (z=0) concentration of the solute. The boundary conditions at the inlet (z=0) and the outlet (z=L) are the 'close-end' boundary conditions commonly used for modeling mass transport in packed beds. The zero derivative at r=0 arises from the symmetry or equivalently no sink condition, and the boundary condition at the pore boundary (r=R) assumes rapid adsorption of BAK to the pHEMA matrix. The initial condition assumes that the concentration of surfactant is zero before the BAK solution is pushed through.

The above model applies the following assumptions and simplifications: the swelling of the plug (if any) is neglected because in the short duration of flow, about 3 s, which is the target time for drop formation; and rapid binding of BAK to the pHEMA matrix occurs at the pore boundary (r=R), which is consistent with the very high partition coefficient of BAK in pHEMA and the 100% removal of BAK in flow experiments, as indicated in the Examples below. The partition coefficient is the ratio of adsorption and desorption rate constants, where very high values can be interpreted as rapid adsorption, with effectively zero concentration at the pore boundary. An approximate solution can be obtained by neglecting diffusive contribution to axial flux, because the convective term is much larger than the diffusion term. This approximation allows the steady state equation in the simplified form:

$$\tilde{u}(r)\frac{\partial c}{\partial \eta} = \frac{DL}{\langle u \rangle R^2}\left[\frac{1}{\zeta}\frac{\partial}{\partial \zeta}\left(\zeta\frac{\partial c}{\partial \zeta}\right)\right] \quad [10]$$

where $$\eta = \frac{z}{L}, \zeta = \frac{r}{R} \text{ and } \tilde{u}(r) = \frac{u}{\langle u \rangle}.$$

The dimensionless parameter $$\frac{DL}{\langle u \rangle R^2}$$

is the ratio of the time required for the fluid to travel through the plug to the time for the BAK molecules to diffuse from the center of the pore to the boundary. When this dimensionless parameter is much smaller than one, the concentration in the pore is equal to the inlet concentration because the fluid travels far too quickly and so molecules do not have adequate time to diffuse radially and adsorb. If the parameter $$\frac{DL}{\langle u \rangle R^2}$$

is much larger than one, the concentration of BAK in the eluting fluid should be zero because the molecules have sufficient time to diffuse in the radial direction and adsorb on the pore walls. By substituting the average velocity from Darcy's law, the requirement for complete removal of BAK from the eluting drop gives the following constraint:

$$\frac{D\mu L^2}{k\Delta P R^2} > 1 \quad [11]$$

This can be simplified by using the Carman-Kozeny equation that gives the following relationship between the hydraulic permeability to the pore size:

$$k = \frac{\varepsilon R^2}{4f} \quad [12]$$

where f is the Kozeny factor, which depends weakly on the porosity (ε), $f=3.4(1-\varepsilon)^{0.175}$. To simplify this analysis, a constant value of 3 is used for f. By substituting this calculated k into the Equations 2 and 11 with known values of various physical and transport properties (μ, D) and other parameters that are required to be fixed by the design criteria (ΔP, τ, $V_d$), the following constraints result:

$$\frac{AR^2}{L} = \frac{4\mu V_d}{\tau\Delta P\varepsilon} \text{ and} \quad [13]$$

$$\frac{R^2}{L} < \sqrt{\frac{12\mu D}{\Delta P\varepsilon}} \quad [14]$$

for the instillation of a single drop of the formulation. If multiple drops are instilled, the fraction of BAK removed in the plug will decrease with volume instilled because of the saturation of the plug with BAK. In these calculations, targeted removal is at least 90% BAK even from the last drop instilled, which would lead to >95% on considering all the drops instilled. Higher removal fractions can easily be integrated into the model to yield the new predictions. To achieve this target the partition coefficient of the plug must be sufficiently high such that the equilibrium concentration in the solution after the uptake of the entire BAK from the formulation in the gel is less than 10% of the initial BAK concentration. The concentration in the gel after uptake of the entire BAK in the formulation is $$\frac{V_f c_0}{AL(1-\varepsilon)},$$

which adds the following constraint in the design:

$$\frac{V_f c_0}{AL(1-\varepsilon)} < 0.1Kc_0 \quad [15]$$

where $V_f$ is the total volume of the formulation passing through the gel plug and K is the partition coefficient defined as the concentration of BAK in the gel phase divided by the concentration of BAK in the solution phase.

The values of all parameters used in the calculations are listed in Table 1, below, and the design constraints obtained from the model (Equations 13-15) are graphically presented in FIG. 3, as these plots predict, for the design parameters in Table 1 for a plug with length, pore radius and the corresponding hydraulic permeability of the BAK, when the plug area is 78.5 $mm^2$. The actual length of the plug is not necessary equal to L, but can be L/T, where T is the tortuosity and estimated to be 3 by viewing the filter plug as a packed bed of non-uniform spheres. The design constraints suggest that the plug area must be at least 0.258 $mm^2$ and preferably larger. As a reasonable design, if the area equals 78.5 $mm^2$, L should be at least 0.33 cm long. Therefore, therefore, when the filter plug is 0.5 cm in length and 78.5 $mm^2$ in area, the minimum hydraulic permeability of 0.13 Da or a pore diameter of 4 μm is needed.

All of the design parameter estimates are based on integrating the device into commonly used eye drop bottles. By re-designing the bottles, the parameters can be altered to improve the device performance. For example, the pressure available for drop instillation could be significantly increased by changing the material of the eye drop bottle. The area of the plug can be adjusted by changing the bottle tip design.

TABLE 1

Typical values of the parameters used in the design constraints of Eq. 13 to 15

| Parameters | Values |
| --- | --- |
| Size of typical eye drop ($V_d$) | 30 μL |
| Total volume of solution in bottle ($V_f$) | 5 mL |
| Viscosity ($\mu$) | 1.0 cP |
| Diffusivity (D) | $10^{-9}$ m$^2$/s |
| Pressure drop ($\Delta P$) | 5000 Pa[a] |
| Typical time to create a drop ($\tau$) | 3 s |
| Porosity ($\varepsilon$) | 0.4 |
| Partition coefficient (K) | 100 |

[a]The value is the estimated typical pressure drop created during the process of applying an eye drop with eye drop bottle.

The porous plug can be included in the package for removal of BAK from commercial formulation. For example, the porous plug can be used with the commercially available glaucoma drugs: Betimol®, which is a clear, isotonic, phosphate buffered aqueous solution containing 0.25% or 0.5% of drug timolol as hemihydrate, 0.01% BAK, and having inactive ingredients that include monosodium and disodium phosphate to adjust pH (6.5-7.5); COSOPT®, which is an isotonic, buffered, slightly viscous, aqueous solution containing a combination of two glaucoma drugs 0.5% timolol, 2% dorzolamide, 0.0075% BAK, and inactive ingredients sodium citrate, hydroxyethyl cellulose, sodium hydroxide, and mannitol; XALATAN®, which is an isotonic, buffered aqueous solution of 0.005% latanoprost, 0.02% BAK, and inactive ingredients sodium chloride, sodium dihydrogen phosphate, and disodium hydrogen phosphate; LUMIGAN® which contains bimatoprost 0.3 mg/m; 0.05 mg/mL BAK, and inactive ingredients sodium chloride, sodium phosphate, and citric acid; and TRAVATAN®, which contains travoprost 0.04 mg/mL, 0.15 mg/mL BAK, and inactive ingredients polyoxyl 40 hydrogenated castor oil, tromethamine, boric acid, mannitol, edetate disodium, sodium hydroxide and/or hydrochloric acid. The plug can also be incorporated into any of the rewetting drop formulations. The above list is a small subset of all ophthalmic drug formulations that can have the preservative removed by integrating the plug with the bottle. The device can be a separate entity that is attached to the formulation dispensing units through suitable connectors.

Although the plugs according to embodiments of the invention are effective for the removal of BAK and other preservatives, the invention is not so limited. Components other than preservatives that are required in the formulation but are not needed inside the body, such as, but not limited to formulation stabilizers and anti-oxidants can be removed. Other fluids can be used where a preservative is selectively removed from a fluid composition. Fluids that can be dispersed from a container through a preservative removing device include intravenous drugs, oral drug solutions and suspensions, foods, beverages, fragrances, lotions, soaps, shampoos, or any other fluid that is to be ingested, contacted with skin, wounds, orifices, or openings made to a body. Although as disclosed herein, the exemplary preservative is BAK, other preservatives commonly dissolved in an aqueous based solution, emulsion, or suspension can be removed from a preservative removing device, adapted to remove a desired preservative.

METHODS AND MATERIALS

Preparation of Macroporous Poly(2-Hydroxyethyl Methacrylate) Hydrogel

Figure 4:
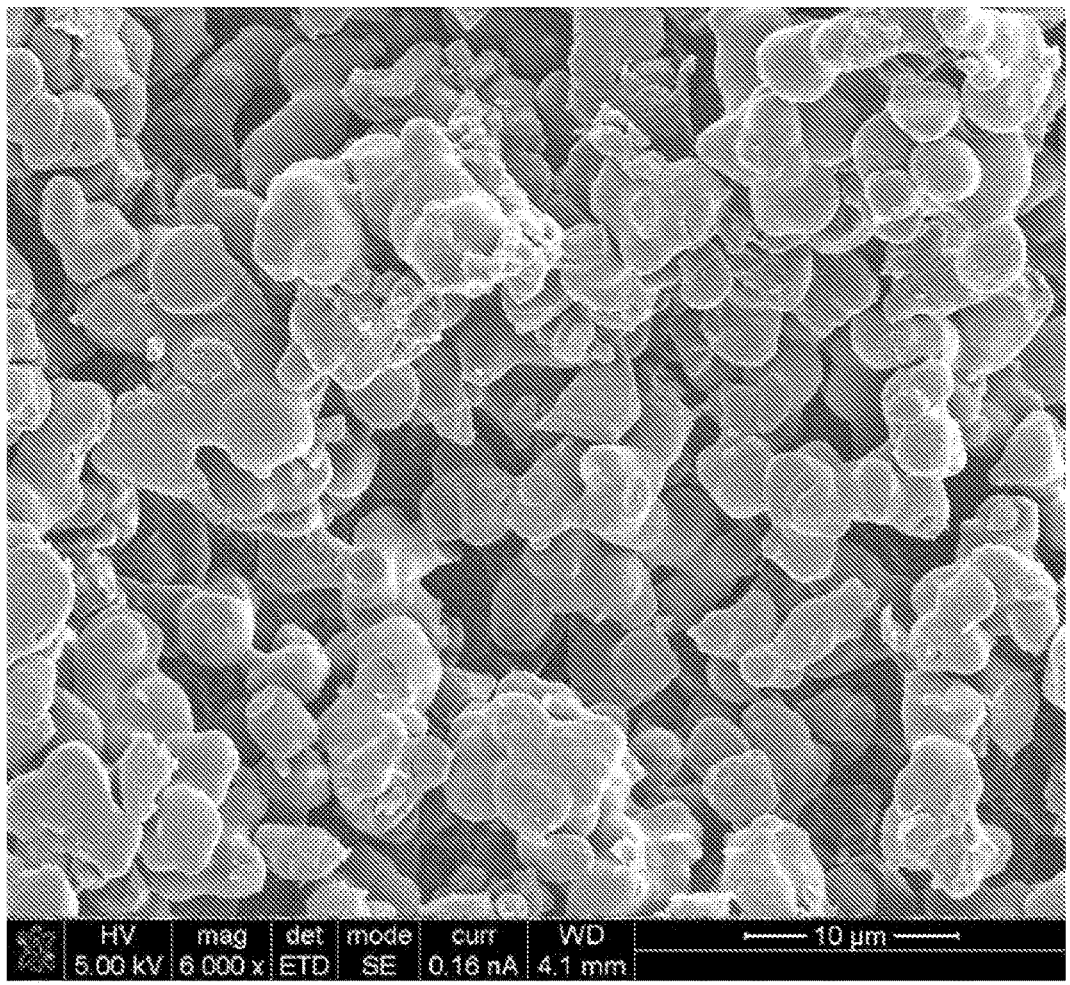
FIG. 4 shows an SEM image of macroporous pHEMA hydrogel.

Macroporous poly(2-hydroxyethyl methacrylate) (pHEMA) hydrogel was prepared by mixing 4 mL of HEMA monomer, 400 μL of ethylene glycol dimethacrylate (EGDMA), 15 mmoles of sodium chloride, 10 mg of diphenyl-(2, 4, 6-trimethylbenzoyl)phosphine oxide (TPO) and 15 mL of deionized (DI) water with magnetic stirring for 20 min at 900 rpm. The mixture was deoxygenated by bubbling pure nitrogen through the mixture for 30 min. The deoxygenated mixture was poured into a 55×17 mm (diameter× height) Pyrex® petri dish, covered to prevent significant evaporation, and irradiated with UV light for 40 min using a UVB-10 transilluminator (ULTRA•LUM, INC, Carson, Calif., USA) with an intensity of 16.50 mW/cm$^2$ sharply peaked at 310 nm. After polymerization, the macroporous pHEMA gel was carefully removed from the petri dish and soaked in 350 mL of DI water for 24 hours to extract unreacted components. The DI water was replaced with fresh DI water every 24 hours for a consecutive of 7 days to thoroughly remove the unreacted components as confirmed by measuring the UV-Vis spectra of the water from the proximity of the gel during the 7 days of extraction where the UV-Vis absorbance was negligible. The synthesized macroporous gel was then storage in DI water. The SEM image of the synthesized pHEMA hydrogel has pore size of few microns, as shown in FIG. 4.

Measurement of Hydraulic Permeability of the Macroporous Gel by Packing in Syringe To determine the pressure applied when a bottle is squeezed, a bottle was held vertically with the exit pointed down and squeezed to determine the mass of liquid that will elute or the number of drops that fall out. The pressure inside the gas phase created by the squeeze can then be determined as $\Delta V/V \times P_{atm}$, where $\Delta V$ is the volume of liquid that elutes out, V is the volume of the gas inside the bottle, $P_{atm}$ is the atmospheric pressure. This method provided an estimate of about 5000 Pa as the pressure generated inside the eye drop bottle during the squeeze. This pressure is not the same as the applied pressure by the fingers. The force/pressure applied by the fingers squeezes the bottles, which in turn reduces the volume inside the bottle. That volume reduction leads to the pressure increase. After determining the available pressure, an estimate of the velocity through the filter based on creation of a drop in about three seconds was carried out. As the required permeability depends on the filter design, the estimates suggest that a hydraulic permeability larger than about 0.1 Da will be adequate with permeability of about 1 Da or larger being more suitable for an eye drop device. Higher values are needed with more viscous solutions, such as wetting drops. While 0.1 Da is adequate for drop dispensing, it is not sufficient for retraction of the fluid remaining in the filter after the drop dispensing.

Figure 5:
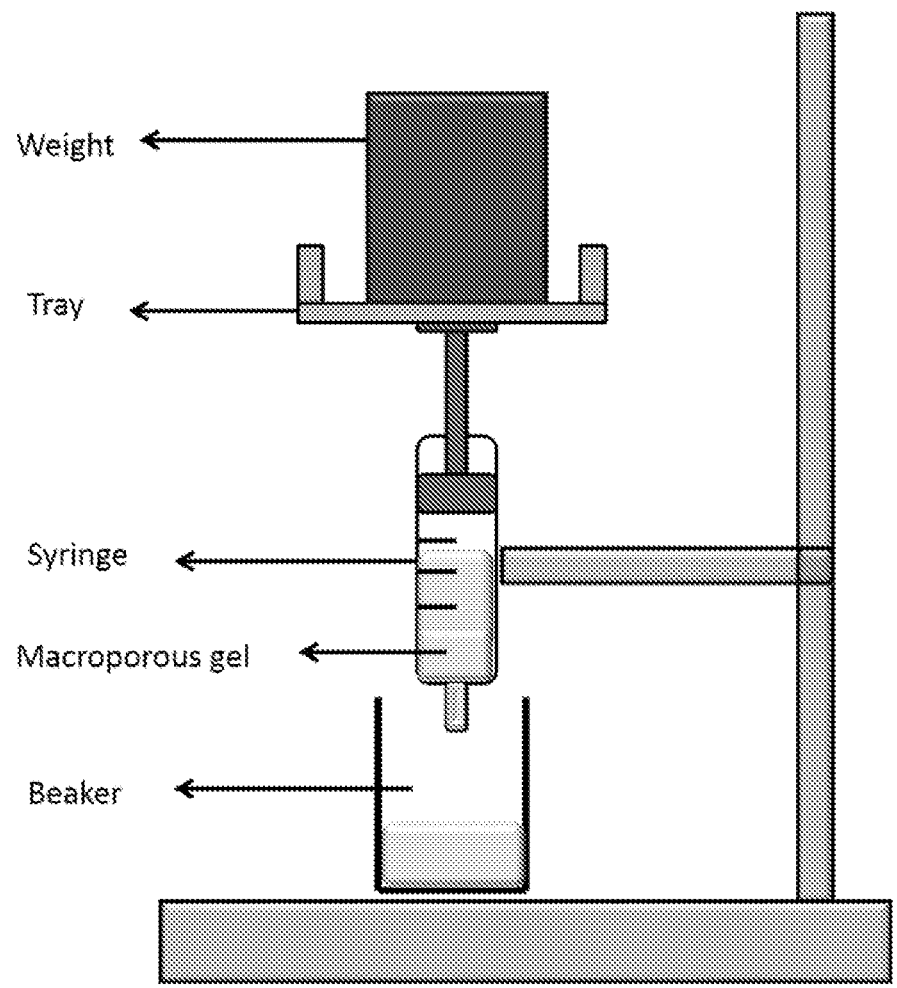
FIG. 5 shows a schematic of the experiment setup for measuring the hydraulic permeability of any material by packing it in a syringe. The syringe is filled with water and then a known force is applied to push out the water.

To test the hydraulic permeability of the matrix, the BAK removal material was packed in a sterile syringe (SOFT-JECT®, 3 ml, Henke-Sass Wolf GmbH, Tuttling, Germany) of 1 cm in diameter. Two pieces of filter papers (Qualitative 1, Whatman®, Maidstone, England) were placed in the syringe to prevent the packed material from leaking out due to the applied pressure. To make the BAK removal material uniformly packed, 2.5 mL of DI water was pushed through the syringe with high pressure each time and repeated at least 5 times. The syringe packed with BAK removal material was used for the hydraulic permeability measurement using the setup was shown in FIG. 5. A beaker was placed immediately below the syringe to collect the outlet solution. The syringe was filled with 2.5 mL of PBS (viscosity=1.00±0.05 cP) and a 1.28 kg ($1.6 \times 10^5$ Pa) weight was placed on the tray to create the pressure drop across the packing. The process was timed using a stopwatch that started with placing the weight on the tray to the time the last drop dropped into the beaker. The weight of the collected PBS solution in the beaker was measured to calculate the flow rate through the filter material. The hydraulic permeability coefficient was then calculated by Darcy's law, Equation 1, above.

Figure 6:
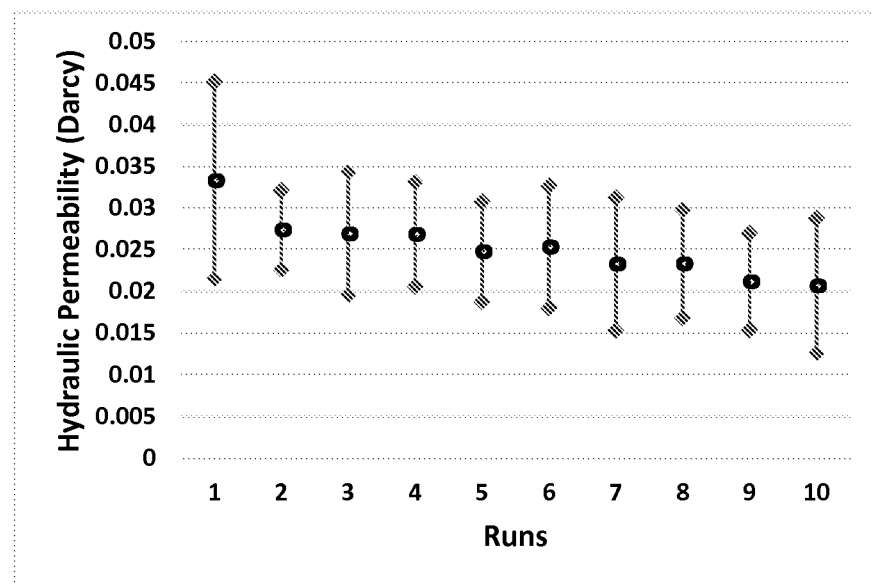
FIG. 6 shows a plot of measured hydraulic permeability for macroporous pHEMA hydrogel packed in a syringe. For each packed sample, the permeability was measured 10 times to determine whether compaction occurs due to flow. The data was measured for 12 independent samples with data points representing the mean±SD for n=12 data points per sample.
Figure 7:
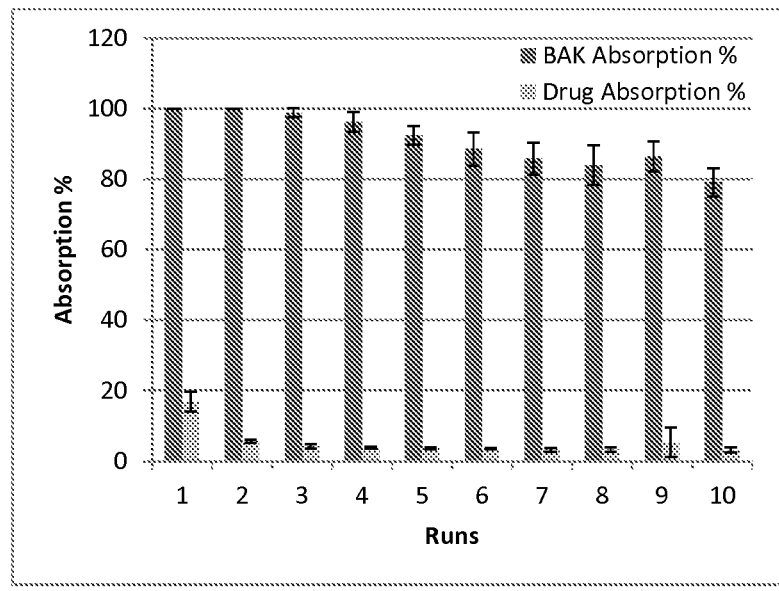
FIG. 7 shows a bar chart of the percentages of BAK and timolol that are removed after passing 2.5 mL of timolol/BAK solution through 5 mm thick macroporous pHEMA gel packed into a 1 cm dia syringe for a series of 10 consecutive passes, where the data are presented as mean±SD with n=3.
Figure 8:
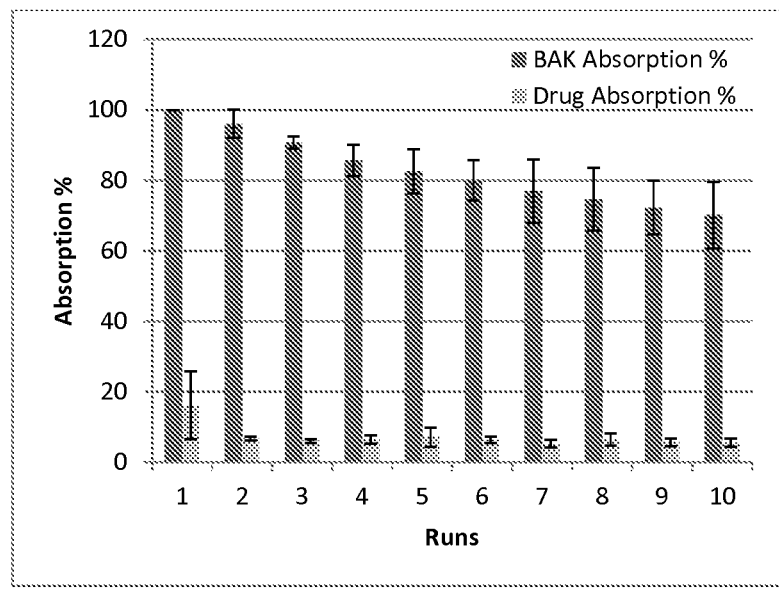
FIG. 8 shows a bar chart of the percentages of BAK and dorzolamide that are removed after passing 2.5 mL of dorzolamide/BAK solution through 5 mm thick macroporous pHEMA gel packed into a 1 cm dia syringe for a series of 10 consecutive passes, where the data are presented as mean±SD with n=3.
Figure 9:
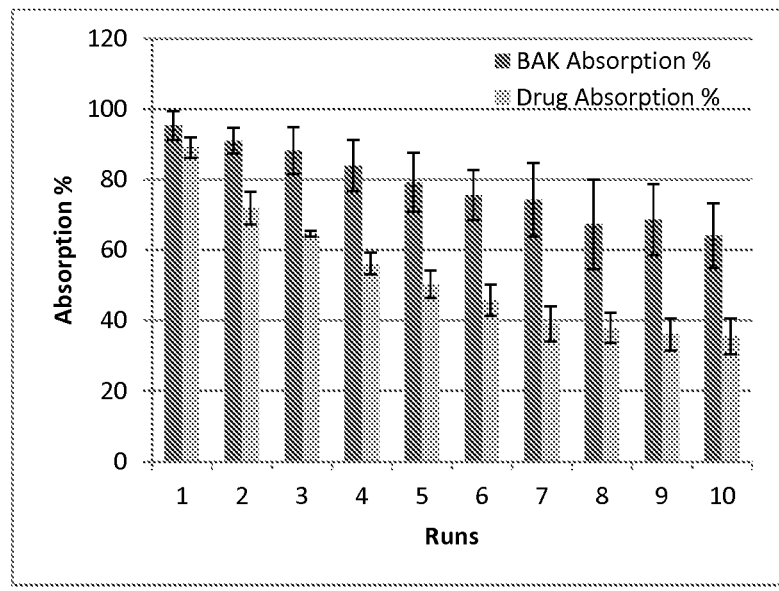
FIG. 9 shows a bar chart of the percentages of BAK and latanoprost that are removed after passing 2.5 mL of latanoprost/BAK solution through a 5 mm thick macroporous pHEMA gel packed into a 1 cm dia syringe for a series of 10 consecutive passes, where the data are presented as mean±SD with n=3.

The hydraulic permeability of the macroporous pHEMA gel prepared as indicated above, was measured 10 times for each of 12 samples, with the resulting permeability shown in FIG. 6. As shown in FIG. 6, the hydraulic permeability of the gel slightly decreased over the measurement, although the trend was not significant. This was due to the high pressure exerting on the gel in each run made the gel pack more tightly. The overall average of the hydraulic permeability is 0.025 Darcy.

Performance Testing of the Macroporous pHEMA Gel as BAK Removal Filter

Figure 3:
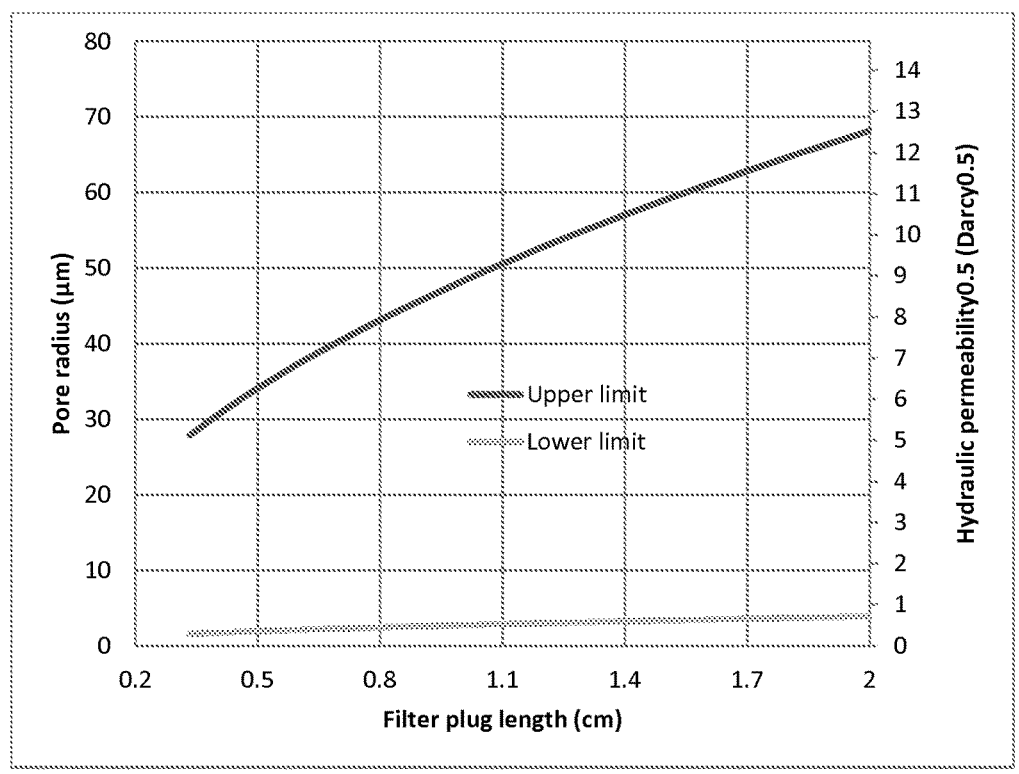
FIG. 3 shows a plot of hydraulic permeability of the BAK filter plug if the plug area is 78.5 mm2 and model predicted design parameters of length, pore radius where the solid lines indicate the upper limit and the minimum requirement of the pore size and the respective hydraulic permeability.

The selectivity of BAK removal was tested with four common ophthalmic drugs including timolol maleate (hydrophilic, medication for glaucoma), dorzolamide hydrochloride (hydrophilic, medication for glaucoma), latanoprost (hydrophobic, medication for glaucoma) and dexamethasone (hydrophobic, medication for infection or eye injuries). The four drugs were dissolved in PBS and mixed with BAK individually. The prepared drug/BAK mixture concentration is summarized in Table 2, below. The macroporous pHEMA hydrogel prepared as above, was used as the BAK removal filter and packed into the syringe, as described above. The experimental setup is that of FIG. 3. A 2.5 mL of drug/BAK solution was placed in the syringe and forced through the filter plug by the pressure drop created by the weight (1.28 kg) on the tray. The solution that passed through the filter plug was collected and the concentration of drug/BAK was determined by measuring the UV-Vis spectra. The detected wavelength range for each drug/BAK mixture is summarized in Table 2, below. The measured UV spectrum was a linear combination of the testing drug and BAK and thus, the individual concentration of the drug and BAK could be determined by applying a least square fit method as described in Kim et al. *Int. J. Pharm.*, 2008, Apr. 2; 353(1-2):205-22 which was validated by comparison to standard mixture solutions of drug and BAK. The same experiment procedure was repeated 10 times for each macroporous pHEMA gel plug. The test solutions contained 0.012 wt % BAK, which was within the normal BAK concentrations, 0.004 wt % to 0.025 wt %, used in commercial eye drops. The drug concentration was adjusted accordingly to the BAK concentration so that the measured UV-Vis spectrum would be significantly different if 100% of the BAK was removed. To be more specific, if 100% of BAK was removed, the UV absorbance at 261 nm, which is the maximum of the BAK spectrum, would decrease by about 50%. The BAK concentration in latanoprost/BAK solution was reduced to 0.003 wt %, which is within the detection limit. The concentration of latanoprost was adjusted such that the UV absorbance in the range of 210-220 nm would decrease by about 50% if all BAK was removed.

FIGS. 7-10 show the percentages of BAK and drug that are absorbed after the mixture solution was passed through the macroporous pHEMA gel plug. As shown in the figures, 100% of BAK was removed by the hydrogel in the first run regardless of the drug in the mixture. The BAK removal percentages decreased after each subsequent pass due to the gel becoming slowly saturated with BAK and removal decreased to 70-80% at the $10^{th}$ pass. For hydrophilic drugs, such as timolol (FIG. 7) and dorzolamide (FIG. 8), the drug adsorption percentages was low, and remained about 5% after the first pass through the $10^{th}$ pass. Macroporous pHEMA hydrogel exhibited an excellent BAK removal efficiency with little hydrophilic drug uptake. However, the drug absorption percentages were as high as 90 and 65% in the first run for hydrophobic drugs of latanoprost (FIG. 9) and dexamethasone (FIG. 10), respectively. The absorption percentage decreased rapidly to 30% and 10% by the $10^{th}$ pass through the gel for latanoprost and dexamethasone, respectively; which suggested that one may pre-equilibrate the macroporous pHEMA gel with drug solution to allow the gel to absorb BAK without uptake of any additional drug.

TABLE 2

Summary of the drug/BAK mixture concentrations as prepared and the UV-Vis wavelength detection range used for testing the separation selectivity

|  | Timolol | Dorzolamide | Latanoprost | Dexamethasone |
|---|---|---|---|---|
| Drug concentration (mg/ml) | 0.01 | 0.005 | 0.03 | 0.005 |
| BAK concentration (mg/ml) | 0.12 | 0.12 | 0.03 | 0.12 |
| Wavelength of UV-Vis (nm) | 261-309 | 231-279 | 210-220 | 237-279 |

*a*PBS was used as the solvent

Measurement of Partition Coefficient of Timolol Maleate, Dorzolamide Hydrochloride, Latanoprost, Dexamethasone and BAK in Macroporous pHEMA Hydrogel As indicated above, the absorption percentage of hydrophilic drug is small, whereas a significant amount of hydrophobic drug is uptake by the macroporous pHEMA gel. The high affinity of hydrophobic drug to the gel can be determined by measuring the partition coefficient of the drug in the gel. To measure the partition coefficient, a piece of macroporous pHEMA gel of 250 mg was soaked in 12 mL of drug or BAK solution. PBS was used as the solvent and the prepared concentrations of the drug and BAK solutions are summarized in Table 3, below. After 15 days of soaking, the concentration of the drug or BAK solution was measured by using UV-Vis spectrophotometry. The drug or BAK concentration after soaking indicated the amount of drug or BAK in reference to the initial concentration is that absorbed into the gel. Partition coefficients calculated from the concentration change is summarized in Table 4, below. The partition coefficient of timolol and dorzolamide in macroporous pHEMA gel is roughly 15 times smaller than that of BAK, which is excellent separation efficiency. In contrast, the partition coefficients of latanoprost and BAK are pretty high and the separation efficiency of the gel for this mixture is poor.

TABLE 3

Concentration of drug and BAK in PBS solutions.

| | Timolol | Dorzolamide | Latanoprost | Dexamethasone | BAK |
|---|---|---|---|---|---|
| Concentration (mg/ml) | 0.08 | 0.07 | 0.04 | 0.07 | 2.4 |

TABLE 4

Partition coefficient of drugs and BAK in macroporous pHEMA gel.

| | Timolol | Dorzolamide | Latanoprost | Dexamethasone | BAK |
|---|---|---|---|---|---|
| Partition coefficient[a] | 6.49 ± 0.37 | 7.59 ± 0.56 | 90.18 ± 1.36 | 33.53 ± 1.31 | 101.61 ± 11.51 |

[a] as mean ± SD with n = 3

Performance Testing of the Macroporous pHEMA Particles for BAK Removal

Macroporous pHEMA hydrogel as prepared above was dried in the oven of 80° C. and crushed into particles and the particles packed into the syringe. Two pieces of filter papers were placed at the bottom of the syringe to prevent the packing particles from leaking out. Particles facilitate packing of a hydrogel into the neck of the eye drop bottle where packing is amenable to high-throughput industrial scale loading of gel filters. To evaluate the performance of the pHEMA particles, the hydraulic permeability and the selectivity of separation of BAK from timolol, dorzolamide, latanoprost and dexamethasone were measured with the same experiment setup shown in FIG. 5. The prepared concentrations of the 4 different drug/BAK mixtures were summarized in Table 2, above. The syringe was filled with 2.5 mL of drug/BAK solution and a beaker was placed below the syringe to collect the outlet solution. A 1.28 kg ($1.6 \times 10^5$ Pa) weight was placed on the tray to create the pressure drop and force the solution through the packing of pHEMA particles. The process was timed using a stopwatch from the moment of placing the weight to the last drop entered the beaker. The weight of the collected solution in the beaker was measured to calculate the flow rate through the pHEMA particles. The hydraulic permeability was calculated by Darcy's law (Eq. 1) where the cross section area of the syringe was 0.785 cm$^2$ and the height of the packed pHEMA particles was 5 mm. Because the concentration of the drug/BAK solution was fairly dilute, the viscosity of the solution was approximated that of pure PBS (1.00±0.05 cP). The UV spectrum of the collected solution was measured and the individual concentration of the drug and BAK were determined by a least square fit method as described in Kim et al., *Int. J. Pharm.* 2008, Apr. 2; 353(1-2):205-22.

BAK has a high partition coefficient of roughly 100 in macroporous pHEMA hydrogel as indicated in Table 4, above. Surprisingly, the BAK removal percentage decreased at an early stage as more drug/BAK solution passed through the macroporous pHEMA hydrogel, as indicated in FIGS. 7-10. To test if the early decrease was due to saturation of the BAK at the surface of the gel due to slow diffusion into the gel particles experimental runs were separated by 24 hours and only 2.5 mL of drug/BAK solution was passed through the particulate plug each day allowing the diffusion of the BAK from the surface into the interior of the gel particles. The hydraulic permeability and selectivity of separation were measured each time the drug/BAK solution passed through the pHEMA particles. After each measurement, the bottom outlet of the syringe was sealed with parafilm to prevent dehydration of the packed pHEMA particles in the manner equivalent to sealing the eye drop bottle with the cap after use.

FIGS. 11-14 show the percentages of BAK and drug absorbed from the solution after each pass through the pHEMA particulate plug. As illustrated in FIGS. 11-14, nearly 100% of containing BAK was removed by the crushed macroporous pHEMA particles for all 10 passes, regardless of the drug in the solution. Hence a 24 hours period between passes allows the dilution of the surface BAK concentration. The time required for equilibration of the gel particles is much less than 24 hours in a practical eye drop application. The pHEMA particles should be able to remove 100% of BAK from the entire content of a typical eye drop container if use by a single patient in a typical prescribed manner. FIGS. 11-14 display an excellent separation efficiency of BAK from all tested drugs. The pHEMA particles used for latanoprost/BAK and dexamethasone/BAK selectivity were equilibrated with the corresponding drug solution in advanced by simply soaking the pHEMA particles in latanoprost/PBS or dexamethasone/PBS solution. Therefore, only a very small portion of latanoprost and dexamethasone were absorbed as the pre-saturation of the drug in the particles, allowed passage of the drug without absorption even though the BAK was effectively partitioned into the pHEMA hydrogel.

Figure 15:
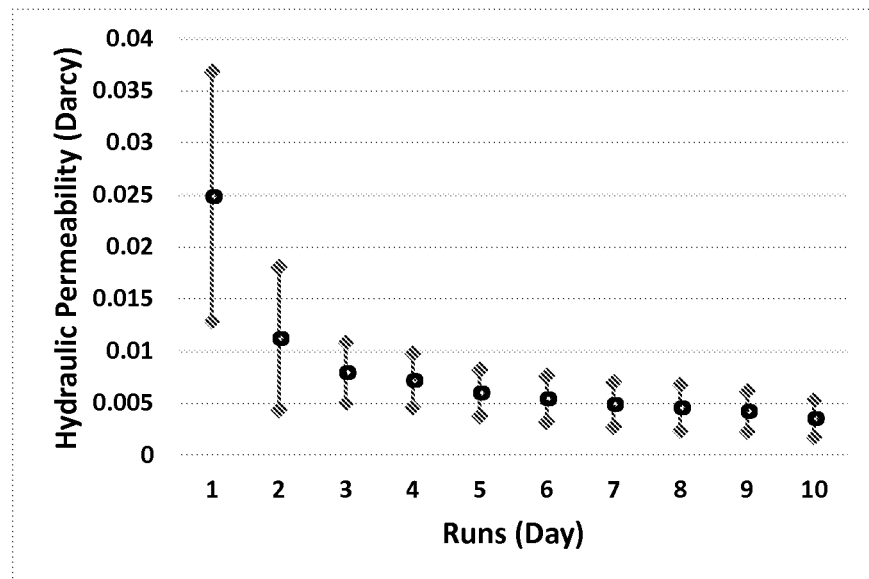
FIG. 15 shows a plot of the hydraulic permeability of crushed macroporous pHEMA particles packed in a syringe with measurements for a series of 10 consecutive passes where each pass is separated by 24 hours, where the data are presented as mean±SD, with n=12.

The hydraulic permeability of the crushed macroporous pHEMA particles is plotted in FIG. 15, where a significant decrease of the average permeability from 0.025 Darcy on day 1 to 0.004 Darcy on day 10. This resulted from the high pressure exerting on the particles for each pass causing the particles to pack more extensively, reducing the volume within the plug for solution flow. For commercial application it is important to prevent decrease in hydraulic permeability with use, which can be achieved by increasing the rigidity of the particles, for example, by increasing the crosslinking density of the gel.

Preparation of Macroporous HEMA-Methacrylic Acid (MAA) Copolymer Hydrogel

As shown in FIGS. 9, 10, 13 and 14, because of the high partition coefficient of hydrophobic drugs in macroporous pHEMA hydrogel, as indicated in Table 4, a significant amount of latanoprost and dexamethasone were removed after passing the drug/BAK solution through the hydrogel. Hydrophilic content of the hydrogel can be increased by addition of comonomers to the polymer, such as, dimethyl acrylamide (DMA), methacrylic acid (MAA), or any other biocompatible, high water content polymer which can result in less affinity for the hydrogel to the hydrophobic drugs.

Figure 10:
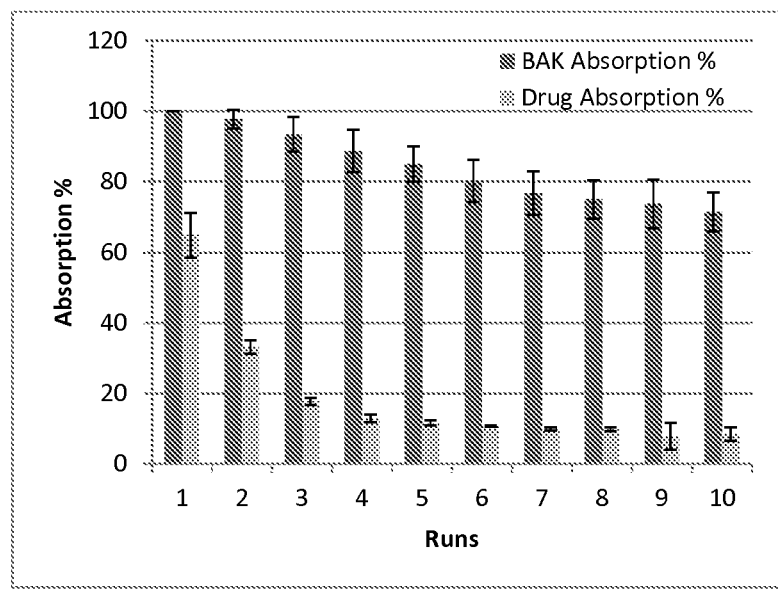
FIG. 10 shows a bar chart of the percentages of BAK and dexamethasone that are removed after passing 2.5 mL of dexamethasone/BAK solution through a 5 mm thick macroporous pHEMA gel packed in a 1 cm diameter syringe for a series of 10 consecutive passes, where the data are presented as mean±SD with n=3.
Figure 11:
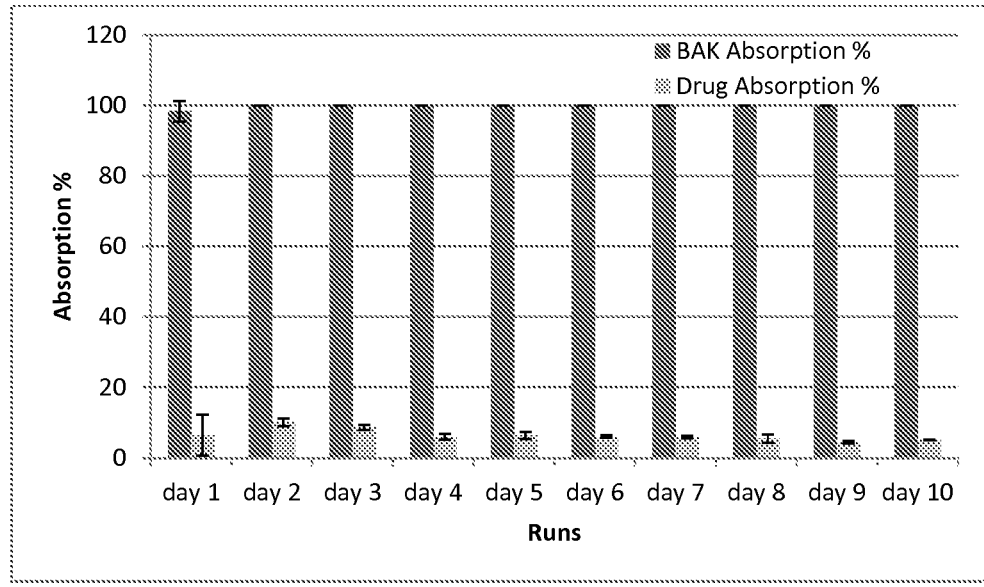
FIG. 11 shows a bar chart of the percentages of BAK and timolol that are removed after passing 2.5 mL of timolol/BAK solution through 5 mm thick plug formed by packing crushed macroporous pHEMA gel in a 1 cm dia syringe for a series of 10 consecutive passes where each pass is separated by 24 hours, where the data are presented as mean±SD with n=3.
Figure 12:
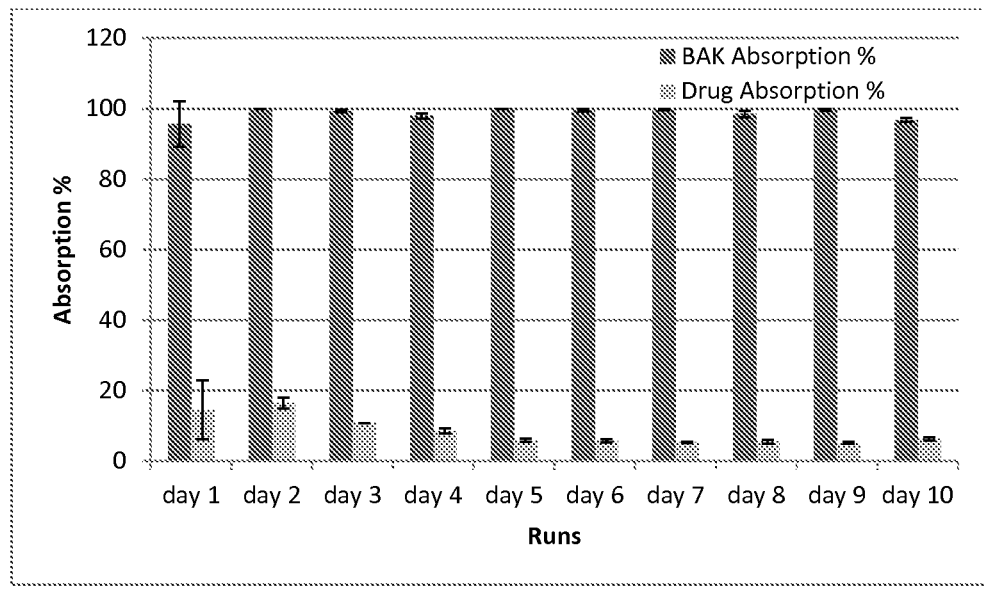
FIG. 12 shows a bar chart of the percentages of BAK and dorzolamide that are removed after passing 2.5 mL of dorzolamide/BAK mixture solution through 5 mm thick plug formed by packing crushed macroporous pHEMA gel in a 1 cm dia syringe for a series of 10 consecutive passes where each pass is separated by 24 hours, where the data are presented as mean±SD with n=3.
Figure 13:
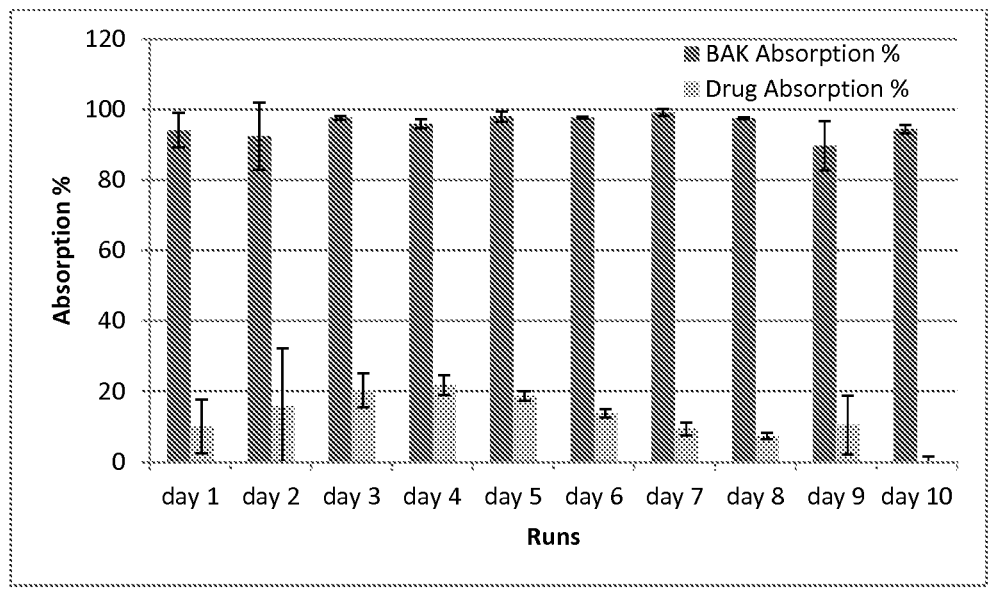
FIG. 13 shows a bar chart of the percentages of BAK and latanoprost that are removed after passing 2.5 mL of latanoprost/BAK solution through 5 mm thick plug formed by packing crushed macroporous pHEMA gel in a 1 cm dia syringe for a series of 10 consecutive passes where each pass is separated by 24 hours, where the data are presented as mean±SD with n=3.
Figure 14:
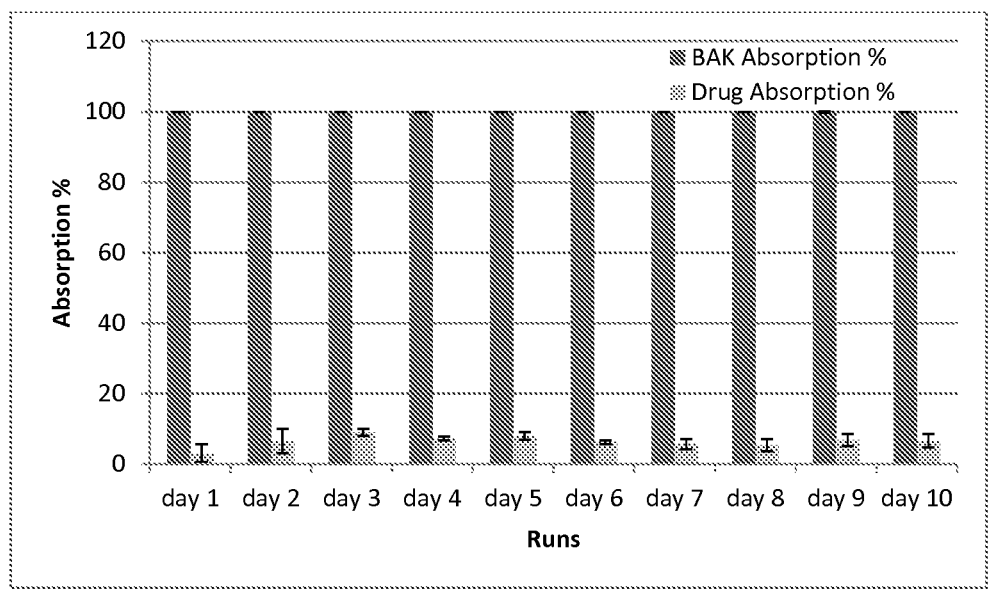
FIG. 14 shows a bar chart of the percentages of BAK and dexamethasone that are removed after passing 2.5 mL of dexamethasone/BAK solution through 5 mm thick plug formed by packing crushed macroporous pHEMA gel in a 1 cm dia syringe for a series of 10 consecutive passes where each pass is separated by 24 hours, where the data are presented as mean±SD with n=3.
Figure 16:
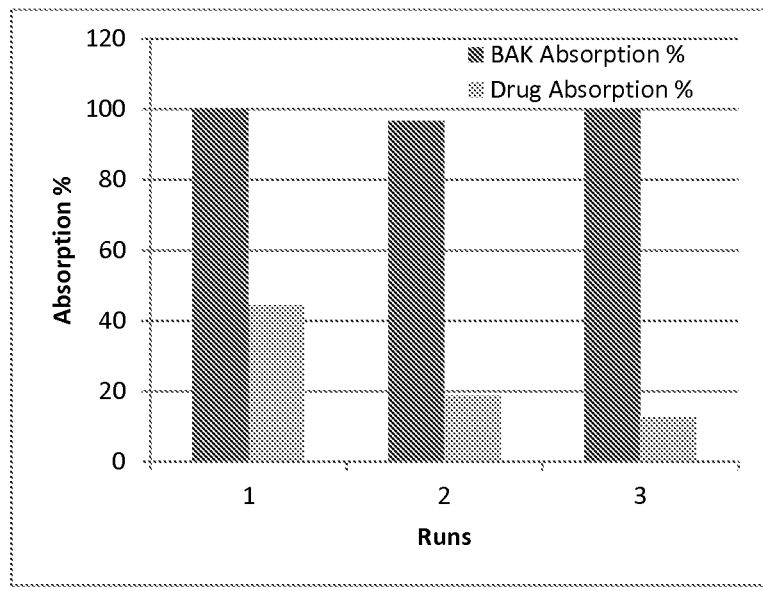
FIG. 16 shows a bar chart of the percentages of BAK and dexamethasone that are removed after pushing 2.5 mL of dexamethasone/BAK mixture solution through a 5 mm thick macroporous HEMA-co-MAA copolymer hydrogel packed in a 1 cm dia syringe, where measurement was repeated 3 times in immediate succession.

To prepare the macroporous HEMA-co-MAA copolymer hydrogel, 3.2 mL of HEMA, 0.4 mL of EGDMA, 0.8 mL of MAA, 4 mmole of sodium chloride, 15 mL of deionized water and 10 mg of TPO were mixed in a glass vial followed by the same steps carried out to form hydrogel, as described above. The resulting hydrogel was subsequently packed into a syringe as described above. A 2.5 mL portion of dexamethasone/BAK solution was passed through the hydrogel to test separation selectivity, and the step of passing was repeated three times on the same hydrogel plug. The height of the packing hydrogel in the syringe was 5 mm. The concentration of the dexamethasone and BAK mixture was 0.005 and 0.12 mg/ml, respectively, and PBS was used as solvent. The results were shown in FIG. 16. As opposed to the macroporous pHEMA hydrogel, as indicated in FIG. 10, the percentage of dexamethasone being absorbed was reduced from 65% to 45% in the first pass.

Figure 17:
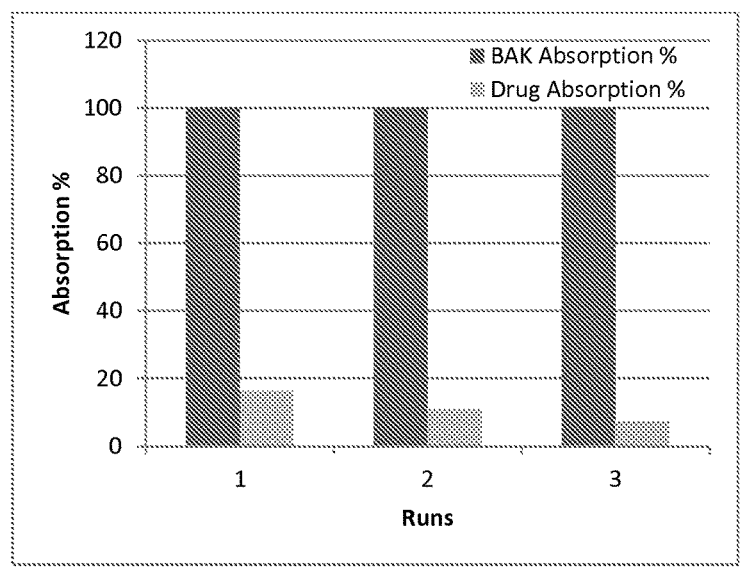
FIG. 17 shows a bar chart of the percentages of BAK and dexamethasone that are removed after pushing 2.5 ml of dexamethasone/BAK mixture solution through the 5 mm thick macroporous pHEMA hydrogel treated with 1% of MAA solution packed in a 1 cm dia syringe, where measurement was repeated 3 times in immediate succession.

Alternately, the macroporous pHEMA hydrogel was prepared by the procedure above followed by soaked into 5%, 2% and 1% MAA solution for 3 hours. DI water was used as the solvent to prepare the MAA solution. A 10 mg quantity of potassium persulfate was added to the solution as a thermal initiator. The hydrogel and the solution were placed in an 80° C. oven overnight. The MAA treated pHEMA hydrogel was taken out of the vial and washed with large quantity of DI water to remove unreacted components. The hydrogel was packed into the syringe as BAK removal filter and its separation efficiency of BAK from dexamethasone was tested in the same manner as the copolymer. The hydraulic permeability of the hydrogel copolymerized with 5% of MAA solution was too low to pass solution through the gel. The separation efficiencies of the hydrogels from 1 and 2% of MAA solution are similar. The result of the hydrogel treated with 1% MAA is shown in FIG. 17. Nearly 100% of BAK was removed in the 3 consecutive runs, while the percentage of dexamethasone being absorbed was diminished to 17% in the first run.

Preparation of pHEMA Particles by Heat-Initiated Polymerization Using EGDMA as the Cross-Linker To a mixture of 1.2 mL of HEMA, 0.3 mL of EGDMA, 12 mL of DI water, and 600 mg of magnesium oxide, 10 mg of benzoyl peroxide was added in a glass vial and the contents magnetic stirring for 20 minutes at 900 rpm. The presence of magnesium oxide caused the mixture to phase separated. Small globules containing HEMA monomer and EGDMA was formed by continuously stirring the system at high rpm. The mixture was deoxygenated with pure nitrogen for 30 min. The mixture was warmed using a water bath at 70° C. for 18 hours with continuous stirring at 900 rpm to retain small globules that polymerize into individual pHEMA particles. After polymerization, pHEMA particles were separated from the mixture solution by vacuum filtration method and washed with a large quantity of DI water to remove unreacted monomers and other impurities and dried in an oven of 80° C.

Figure 18:
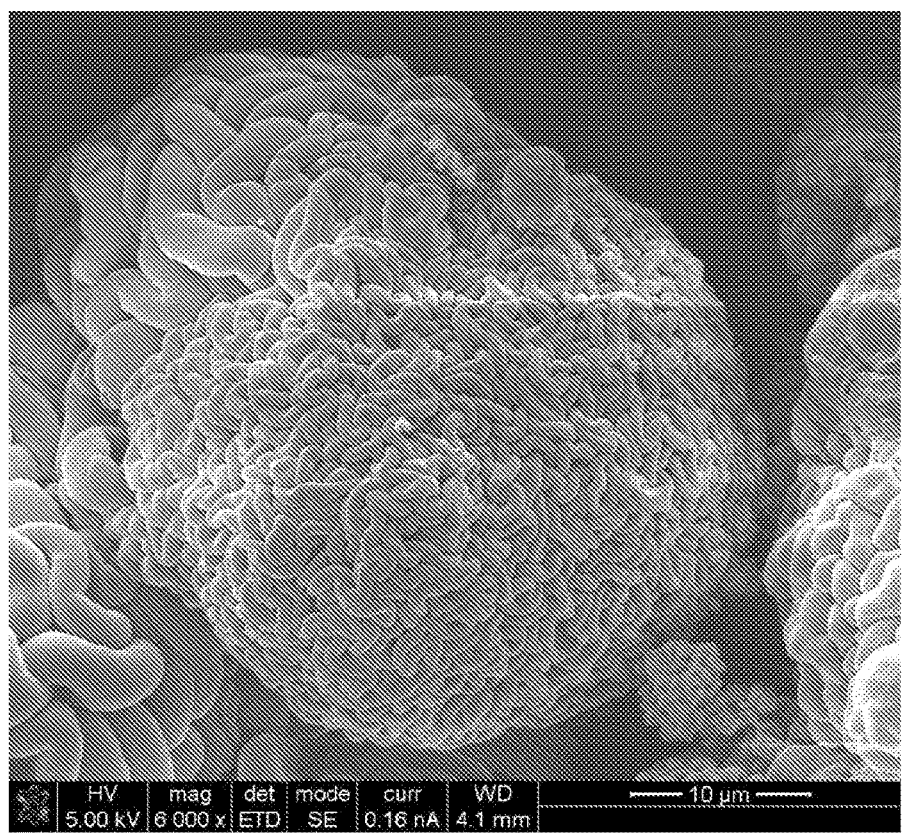
FIG. 18 shows an SEM photographic image of pHEMA particles synthesized by thermally initiated polymerization with EGDMA as cross-linker.

The SEM image of the synthesized pHEMA particles was shown in FIG. 18. The pHEMA particles have wrinkled, "brain-like" surfaces with a large size range from 10 to 300 μm. The particles were packed in the prototype bottle shown in FIG. 19.

Figure 19:
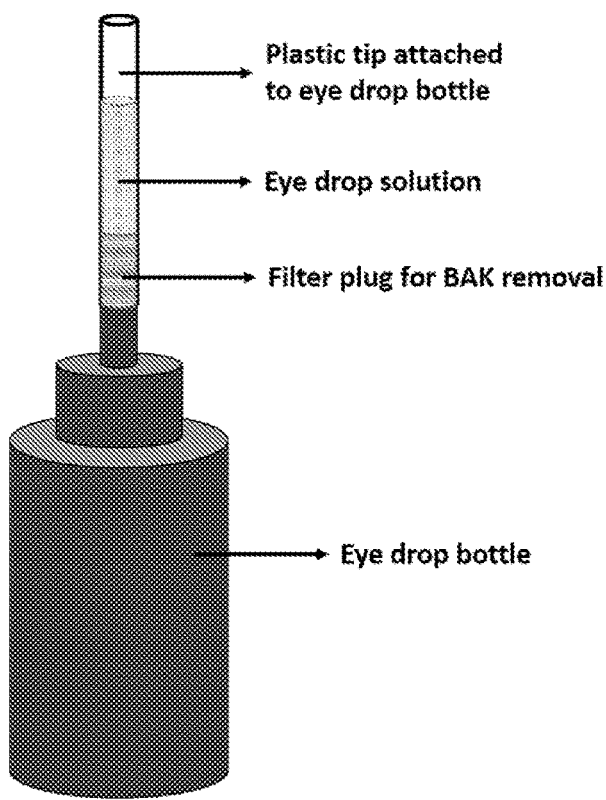
FIG. 19 shows an eye drop bottle prototype packed with BAK removal plug on the tip. The extra space after the plug was kept in this design to facilitate measurement of the hydraulic permeability.

Measurement of Hydraulic Permeability of BAK Filter Packed in an Eye Drop Bottle Prototype FIG. 19 shows a design for an eye drop bottle prototype, which was used to measure the hydraulic permeability of the BAK removal filter packed in the tip. The bottle can be any commercially available eye drop bottle. A section of rigid plastic tube was attached to the tip of the eye drop bottle and the connection part of the bottle to the plastic tube was sealed to prevent leakage. The plastic tube was transparent. Two layers of filter papers are placed at the two ends of the BAK filter plug to prevent the filter plug from being displaced in either direction.

To measure the hydraulic permeability of the packed BAK removal filter, the eye drop bottle was turned upside down and squeezed by fingers to create a pressure drop that forced the eye drop solution into the plastic tube section. Once the applied pressure was removed, the solution flowed back into the bottle. By measuring the flow rate of the solution returning into the bottle, Darcy's law (Eq. 1) was used to calculate the hydraulic permeability of the BAK filter. The exact pressure drop across the filter plug was determined in the following manner. Since the temperature change is negligible and the mass of the gas in the eye drop bottle remains constant before and after the squeezing, we know from the ideal gas law that $$P_0 V_0 = P_f(V_0 + \Delta V) \text{ or } P_f = \frac{P_0 V_0}{V_0 + \Delta V} \qquad \text{Eq. 16}$$

where $P_0$ is the pressure in the eye drop bottle before the bottle is squeezed which also equals to atmospheric pressure, $P_f$ is the pressure in the bottle after the bottle is squeezed, $V_0$ is the gas volume in the bottle before the bottle is squeezed and $\Delta V$ is the volume of solution being pushed out of the bottle. The pressure drop ($\Delta P$) that pushes the solution back would be $$\Delta P(t) = P_0 - P_f(t) = \frac{P_0[\Delta V - V'(t)]}{V_0 + [\Delta V - V'(t)]} \qquad \text{Eq. 17}$$

where V' is the volume of the solution that has already passed through the filter and got back into the bottle. Note that the V' and $\Delta P$ is a function of time. By doing a simple order of magnitude analysis, the effect of gravity force on the solution is sufficiently small than the effect of a pressure drop and hence the influence from gravity is negligible. One can, therefore, rewrite Darcy's law (Eq. 1) as:

$$\frac{dV'}{dt} = \frac{kAP_0}{\mu h} \frac{\Delta V - V'}{V_0 + (\Delta V - V')}, \qquad \text{Eq. 18}$$

where k is the hydraulic permeability, p is the viscosity of the solution and h is the length of the filter plug. This is an ODE equation and V' can be easily solved as a function of time. The equation can be further simplified because V' is much smaller than $V_0 + \Delta V$ and thus Eq. 18 becomes:

$$\frac{dV'}{dt} = \frac{kAP_0}{\mu h} \frac{\Delta V - V'}{V_0 + \Delta V} \qquad \text{Eq. 19}$$

with the initial condition of $$t=0, V'=0. \qquad \text{Eq. 20}$$

The solution to Eq. 19 and 20 is $$V' = \Delta V \left[ 1 - \exp\left( -k \frac{AP_0}{\mu h (V_0 + \Delta V)} t \right) \right]. \qquad \text{Eq. 21}$$

The eye drops bottle Systane® was used. The weight of the empty bottle was measured to be roughly 5.5 grams. The bottle was then filled with water and the total mass was 22.5 grams. Subsequently, 12 grams of water was squeezed from the bottle so that $V_0$ would be roughly 12 mL and the water left in the bottle is roughly 5 mL. The filter material prepared by thermal initiation, as disclosed above, was used and the packing length is 8 mm. The cross area of the plastic tube was 0.0314 cm$^2$ and the viscosity of water at 20° C. is about 1.002×10$^{-3}$ Pa·s.

Figure 20:
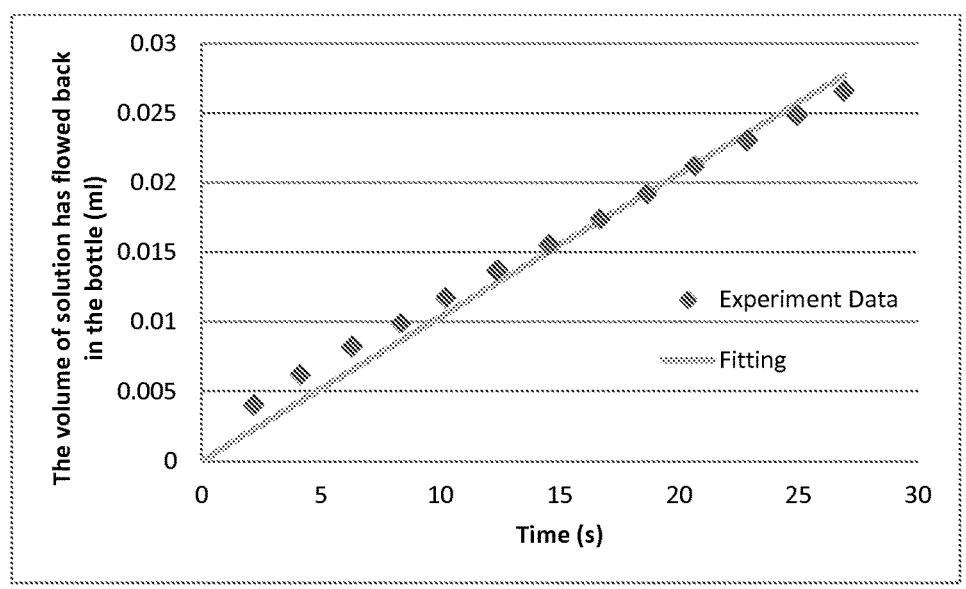
FIG. 20 shows a plot of the total flowrate from the bottle containing the plug as a function of time. The hydraulic permeability was calculated by fitting the data to the theoretical equation.

An eye drop bottle was turned upside down to squeeze out 1.5 mL of water ($\Delta V$). This relatively large volume, 1.5 mL, of water creates a sufficient pressure drop to draw the water back at a reasonable flow rate allowing the simplification from Eq. 18 to Eq. 19 with sufficient accuracy. The process of water flowing back into the eye drop bottle was filmed where from V' as a function of time was analyzed. The above model (Eq. 21) was used to fit the experiment data (V' vs. t) to determine the hydraulic permeability (k) by using the function "fminsearch" in MATLAB®. The fit to the model is reasonably good and the result is shown in FIG. 20. The hydraulic permeability was determined to be 0.0459 Darcy.

Selective BAK Removal by Crushed Macroporous pHEMA Particles Integrated into Eye Drop Bottle Prototype The crushed macroporous pHEMA particles were prepared as described above. The particles were packed in the eye drop bottle prototype (FIG. 19) to test its selectivity of separation of BAK from latanoprost. The concentration of latanoprost and BAK prepared for the testing were both 0.03 mg/mL with PBS as the solvent. The drug/BAK solution was injected into the prototype bottle with a syringe. A clip was clipping on the bottle to create a constant pressure drop across the packing pHEMA particles of 8 mm in length. A volume of 1.5 mL of the drug/BAK solution was passed through the filter by squeezing the bottle. The UV spectrum of the outlet solution was measured and the individual concentration of the drug and BAK was determined by a least square fit method as described in Kim et al., *Int. J. Pharm.*, 2008, Apr. 2; 353(1-2):205-22. The tip of the prototype bottle was sealed with parafilm. After 24 hours, another 1.5 mL drug/BAK solution was removed through the same filter and again to measure the concentrations of the drug and BAK. The step was repeated 10 times over a total of 10 days.

Figure 21:
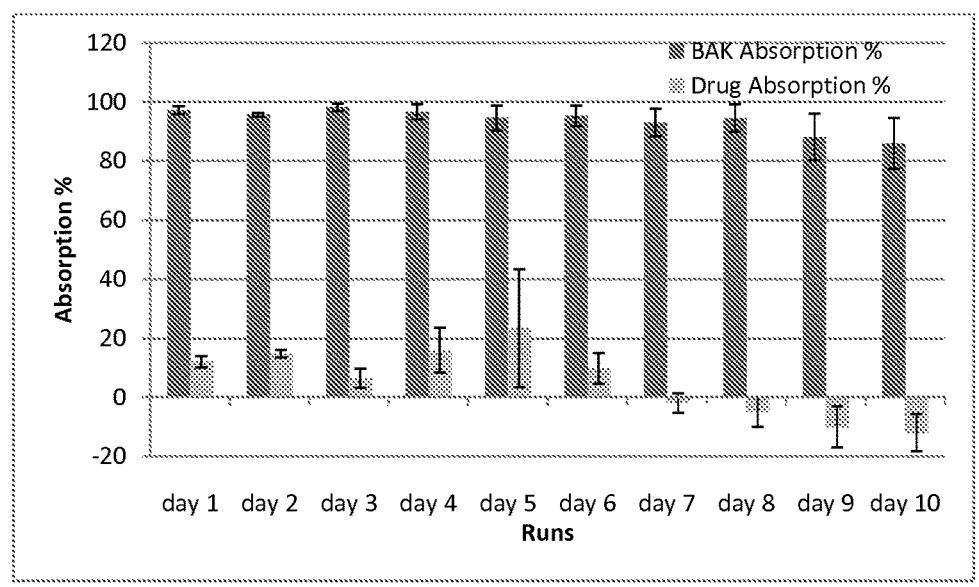
FIG. 21 shows a bar chart of the percentages of BAK and latanoprost that are removed after passing 1.5 mL of a latanoprost/BAK solution through 8-mm thick crushed macroporous pHEMA particles packed in the tip of the eye drop prototype for 10 daily runs over 10 days where the data points are mean±SD with n=3.

FIG. 21 showed the percentages of BAK and latanoprost absorbed after the mixture solution flowed through the pHEMA particles. The pHEMA particles had been pre-equilibrated with the latanoprost as described above to suppress the amount of drug absorbed. Nearly 100% of containing BAK was removed by the particles in all 10 runs.

Selective BAK Removal by pHEMA Particles Prepared by UV-Initiated Polymerization Using EGDMA as the Cross Linker Integrated into Eye Drop Bottle Prototype As shown in FIG. 15, the plug of crushed macroporous pHEMA hydrogel has a very low hydraulic permeability. Alternatively, pHEMA particles were prepared photo chemically where 1.2 mL of HEMA, 0.3 mL of EGDMA, 12 mL of DI water, 900 mg of sodium chloride and 10 mg of TPO initiator were mixed in a glass vial and magnetic stirring for 20 minutes at 900 rpm. The sodium chloride promoted phase separation of the mixture. Small globules containing HEMA monomer and EGDMA was formed by continuously stirring the system at high rpm. The mixture was then deoxygenated using pure nitrogen for 30 min. The mixture was poured into a 55×17 mm (diameter×height) Pyrex® petri dish and irradiated with UV light for 2 hours by a UVB-10 transilluminator (ULTRA•LUM, INC, Carson, Calif., USA) with an intensity of 16.50 mW/cm$^2$ sharply peaked at 310 nm. During the UV curing, the mixture was continuously stirred by a 35×6 mm magnetic stirring bar at 70 rpm so that the small globules would remain separated and polymerize into individual pHEMA particles. In addition, the petri dish was covered to avoid water evaporation and oxygenation. After the polymerization, the pHEMA particles were separated from the solution by vacuum filtration method and washed with a large quantity of DI water to remove the unreacted monomers and other impurities. The particles were then dried in an oven of 80° C.

An SEM image of the synthesized pHEMA particles is shown in FIG. 20. The pHEMA particle size has a wide range, from 10 to as large as 200 µm, which have a spherical shape with a smooth surface. The synthesized particles were packed in the prototype bottle and tested for their selectivity of separation of BAK from timolol. The length of the plug of the packed particles was 8 mm. The timolol and BAK concentration prepared for the testing were 0.01 and 0.12 mg/mL, respectively, with PBS as the solvent. The drug/BAK solution was injected into the prototype bottle with a syringe. A clip was applied to the bottle to impose a constant pressure drop. A 1.5 mL aliquot of the drug/BAK solution was forced through the filter by squeezing the bottle. The UV spectrum of the outlet solution was measured and the concentrations of the drug and BAK were determined by the least square fit method described in Kim et al., *Int. J. Pharm.*, 2008, Apr. 2; 353(1-2):205-22. Five samples were successively removed through the plug.

Figure 23:
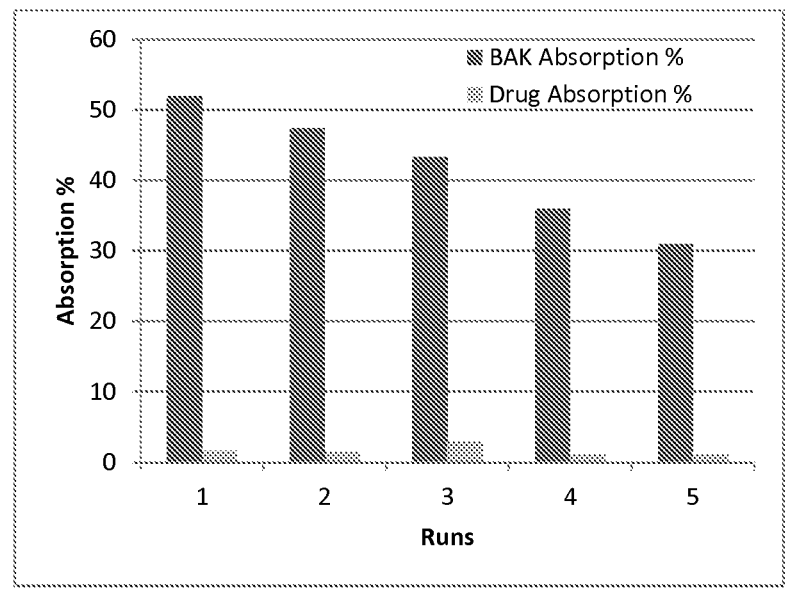
FIG. 23 is a bar chart of the percentages of BAK and timolol that are removed after passing the timolol/BAK solution through 8-mm thick plug of pHEMA particles prepared by photo-polymerization packed in the tip of the eye drop prototype bottle with 1.5 mL of drug/BAK solution passing through the plug for each of 5 passes in immediate succession.

FIG. 23 showed the percentages of BAK and timolol that absorbed in the filter from the mixture after each aliquot was passed through the pHEMA particles. Roughly 50% of BAK was removed by the pHEMA particles in the first pass, while only 30% was removed on the 5$^{th}$ run. Only about 1.5% of the timolol were removed by the pHEMA particles in each of the 5 runs.

Figure 22:
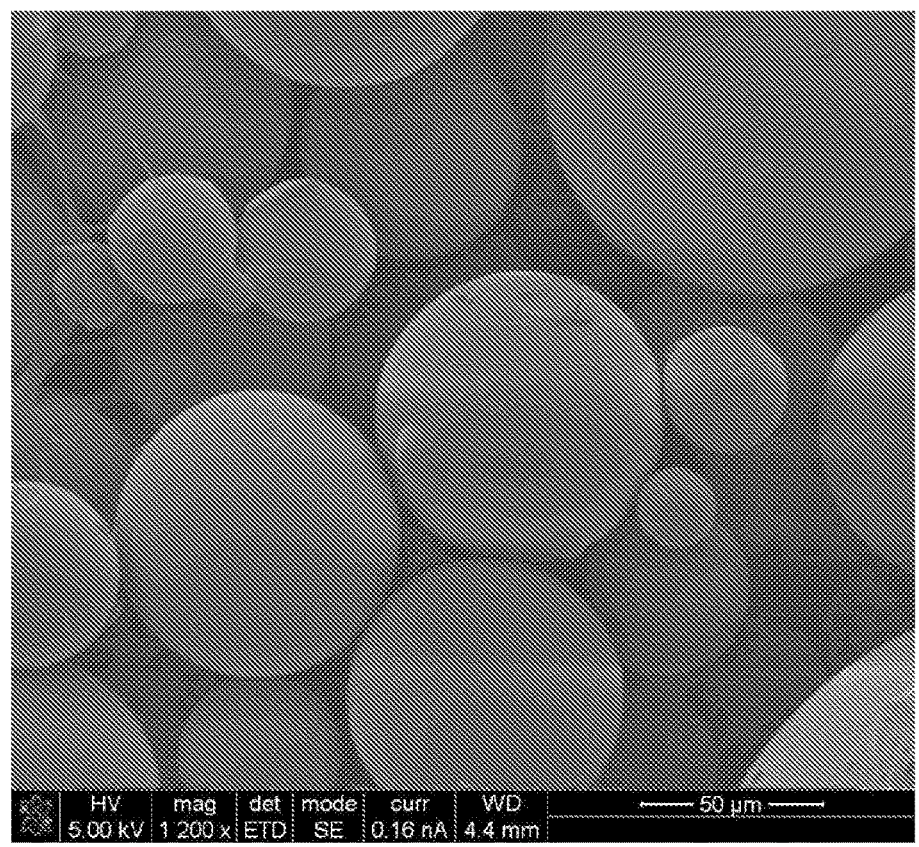
FIG. 22 shows a SEM image of pHEMA particles synthesized by UV polymerization using EGDMA as cross-linker, where the pHEMA particle size ranges from 10 to 200 µm with near spherical particles with smooth surface.
Figure 24:
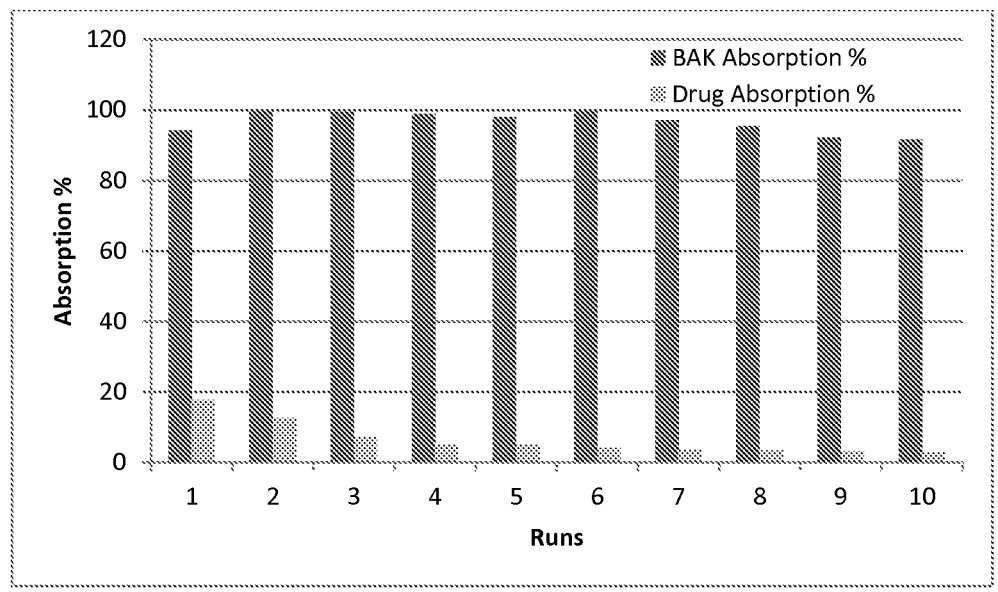
FIG. 24 is a bar chart plot of the percentages of BAK and timolol that are removed after passing a timolol/BAK solution through 8-mm thick plug of pHEMA particles prepared by heat-initiated polymerization packed in the tip of an eye drop prototype bottle, where 1.5 mL of drug/BAK solution was passed through the packing in each run for 10 passes in immediate succession.

Performance Testing of pHEMA Particles Prepared by Heat-Initiated Polymerization as BAK Removal Filter Integrated into Eye Drop Bottle Prototype FIG. 24 indicates the percentages of BAK and timolol that were absorbed after the mixture in solution was passed through the heat-initiated pHEMA particles, shown in FIG. 18. As shown in FIG. 24, nearly 100% of the BAK was removed by the particles in each of 10 passes that were carried out successively. About 17% of timolol was removed in the 1st run while the amount removed reduced to about 3% in the 10$^{th}$ run. The hydraulic permeability of the packing particles is 0.0459 Darcy which was measured as described, above. Due to the increased particle size, the hydraulic permeability is significantly improved when compared to that of the particles prepared by crushing the macroporous pHEMA hydrogel. The size of the particles prepared by UV or heat-initiated polymerization is similar. However, in contrast to the particles with the smooth surface prepared by UV-initiated polymerization, as shown in FIG. 22, the heat initiated polymerization method produces wrinkled, "brain-like" structures, as shown in FIG. 18, which provides a large surface area for absorbing BAK, allowing a much higher BAK removal efficiency. Selectivity for the separation of BAK from timolol was tested. The timolol and BAK concentration prepared for the testing were 0.01 and 0.12 mg/mL, respectively, with PBS as the solvent. The drug/BAK solution was injected into the prototype bottle with a syringe. A clip was clipping on the bottle to create a constant pressure drop across the 8 mm height of packing. 1.5 mL of the drug/BAK solution was pushed through the filter by squeezing the bottle. The UV spectrum of the outlet solution was measured and the individual concentration of the drug and BAK was determined by a least square fit method as described in Kim et al., *Int. J.*

Pharm., 2008, Apr. 2; 353(1-2):205-22. This step was repeated 10 times immediately on the same filter sample without waiting.

Performance Testing of pHEMA Particles Prepared by Using Trimethylolpropane Ethoxylate Triacrylate as Cross-Linker More rigid and larger size particles create a larger void space for fluid to flow and improved hydraulic permeability. If the particles hydrate significantly, the void volume and hydraulic permeability will change significantly depending on the degree of hydration. This would be undesirable because the plug is drug at the time of the installation of the first drop but then could be partially or fully hydrated for subsequent instillations, depending on whether the plug retains the fluid in the interim time between successive instillations. Trimethylolpropane ethoxylate triacrylate (SR454HP or SR9035) was added to the pHEMA particles formulation as cross-linker. pHEMA particles were prepared photochemically where 1.4 mL of HEMA, 0.1 mL of trimethylolpropane ethoxylate triacrylate, 12 mL of DI water, and 10 µL of 2-hydroxy-2-methyl-1-phenyl-propan-1-one were mixed in a glass vial and magnetic stirring for 20 minutes at 900 rpm. The mixture was deoxygenated using pure nitrogen for 30 min. The mixture was poured into a 55×17 mm (diameter×height) Pyrex® petri dish and irradiated with UV light for 2 hours by a UVB-10 transilluminator with an intensity of 16.50 mW/cm$^2$ sharply peaked at 310 nm. During the UV curing, the mixture was continuously stirred by a 35×6 mm magnetic stirring bar at 70 rpm. In addition, the petri dish was covered to avoid water evaporation and oxygenation. After polymerization, the pHEMA gel were separated from the solution by vacuum filtration method and washed with a large quantity of DI water to remove the unreacted monomers and other impurities. The pHEMA gel was then dried in an oven of 80° C. and crushed into particles in a mortar.

Figure 25:
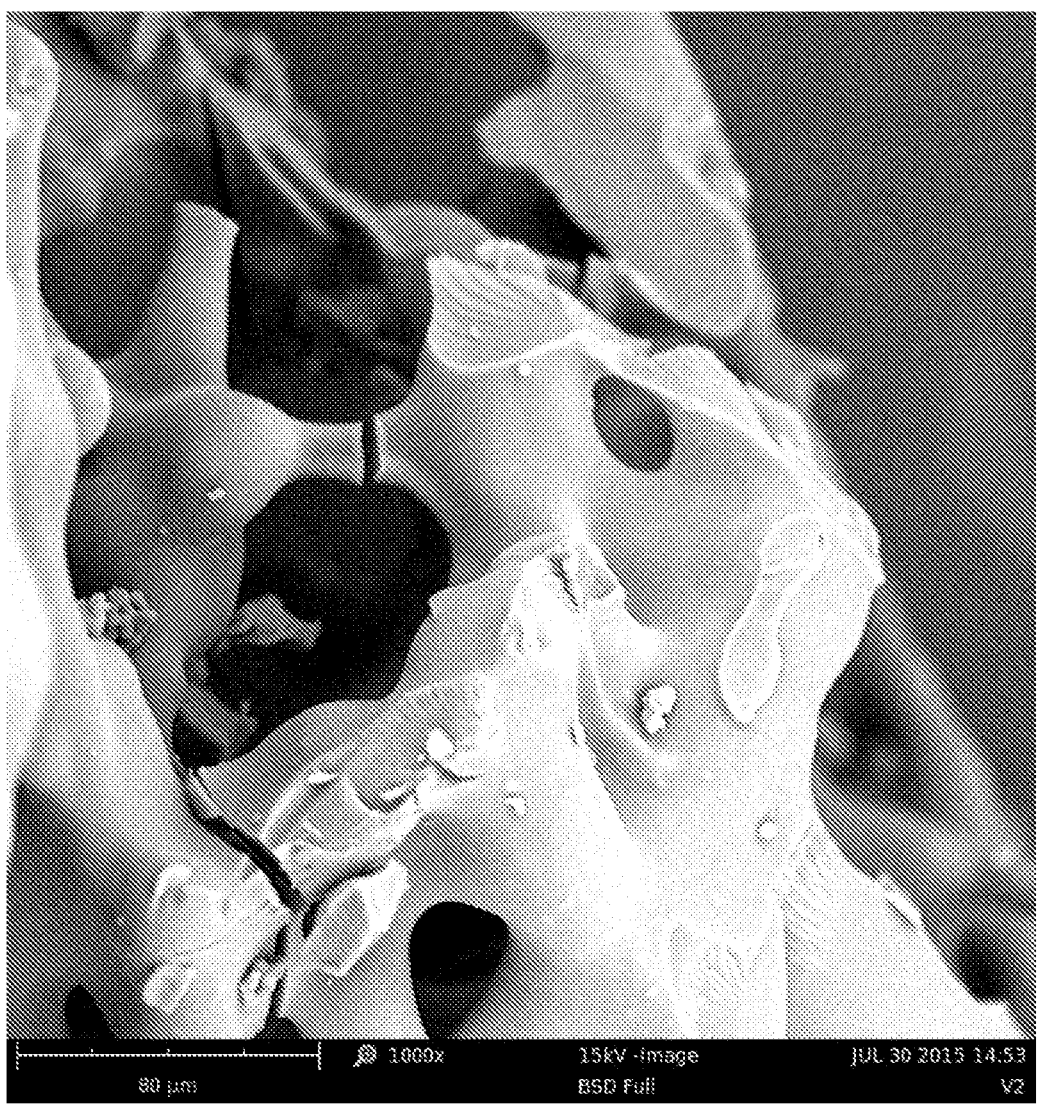
FIG. 25 shows the SEM image of pHEMA particles prepared by UV polymerization using SR454HP as cross-linker.

The SEM image of the synthesized pHEMA particles is shown in FIG. 25. The pHEMA particle size has a wide range, from 30 to as large as 900 µm, and has a highly irregular shape. The synthesized particles were packed in the prototype bottle and tested for their hydraulic permeability, as described above. The length of the plug of the packed particles was 1.8 cm. The measured hydraulic permeability of dried particles prepared using SR454HP as cross-linker is 4.95±0.91 Da (n=3); whereas the hydraulic permeability of hydrated particles reduced to 2.34±0.39 Da (n=3). The measured hydraulic permeability of dried particles prepared using SR9035 as cross-linker is 4.10±0.26 Da (n=3); whereas the hydraulic permeability of hydrated particles reduced to 1.22±0.33 Da (n=3). Compared to the particles prepared by other formulation, as described above, the hydraulic permeability significantly increased more than 25 times, which particles are thus suitable for removing BAK from formulation that has a high viscosity, such as carboxymethyl cellulose (CMC) lubricant eye drops. The high permeability likely arises from the large size and the irregular shape. The irregular shape with sharp edges can prevent drainage of the fluid from the plug back into the container after the applied pressure is removed and thus keeping the plug hydrated. It is important to minimize evaporation from the bottle. When water evaporation is critical, a layer of a hydrophobic particles could be placed at the top of the BAK removing particles as an extra barrier.

The partition coefficients of timolol, CMC and BAK in pHEMA particles prepared using SR9035 as cross-linker was measured. pHEMA particles (100 mg) were soaked in 3.5 mL of timolol, CMC and BAK solution, which concentration was 0.08 mg/mL, 0.5% and 2.4 mg/mL, respectively. After 9 days of soaking, the concentration of the drug or BAK solution was measured by using UV-Vis spectrophotometry. The drug or BAK concentration after soaking indicated the amount of drug or BAK that absorbed into the gel relative to the initial concentration. Partition coefficients calculated from the concentration change are summarized in Table 5, below. The partition coefficient of timolol and CMC in pHEMA particles is much smaller than that of BAK, and should have excellent separation efficiency.

TABLE 5

Partition coefficient of drugs and BAK in pHEMA particles prepared by using SR9035 as cross-linker.

|  | Timolol | CMC | BAK |
| --- | --- | --- | --- |
| Partition coefficient | 5.59 ± 0.13[a] | <1 | ~300 |

[a] as mean ± SD with n = 3

Selectivity of the separation of BAK from timolol was measured. The timolol and BAK concentration were 0.01 and 0.12 mg/mL, respectively, with PBS as the solvent. A constant pressure drop was applied across the packed particles to maintain a constant flow rate through the plug. A 1.5 mL aliquot of the drug/BAK solution was forced through the filter by squeezing the bottle. The UV spectrum of the outlet solution was measured and the concentrations of the drug and BAK were determined by the least square fit method described in Kim et al., Int. J. Pharm., 2008, Apr. 2; 353(1-2):205-22. The tip of the prototype bottle was sealed with parafilm. After 24 hours, another 1.5 mL drug/BAK solution was removed through the same filter and again to measure the concentrations of the drug and BAK. The step was repeated 10 times over a total of 10 days.

Figure 26:
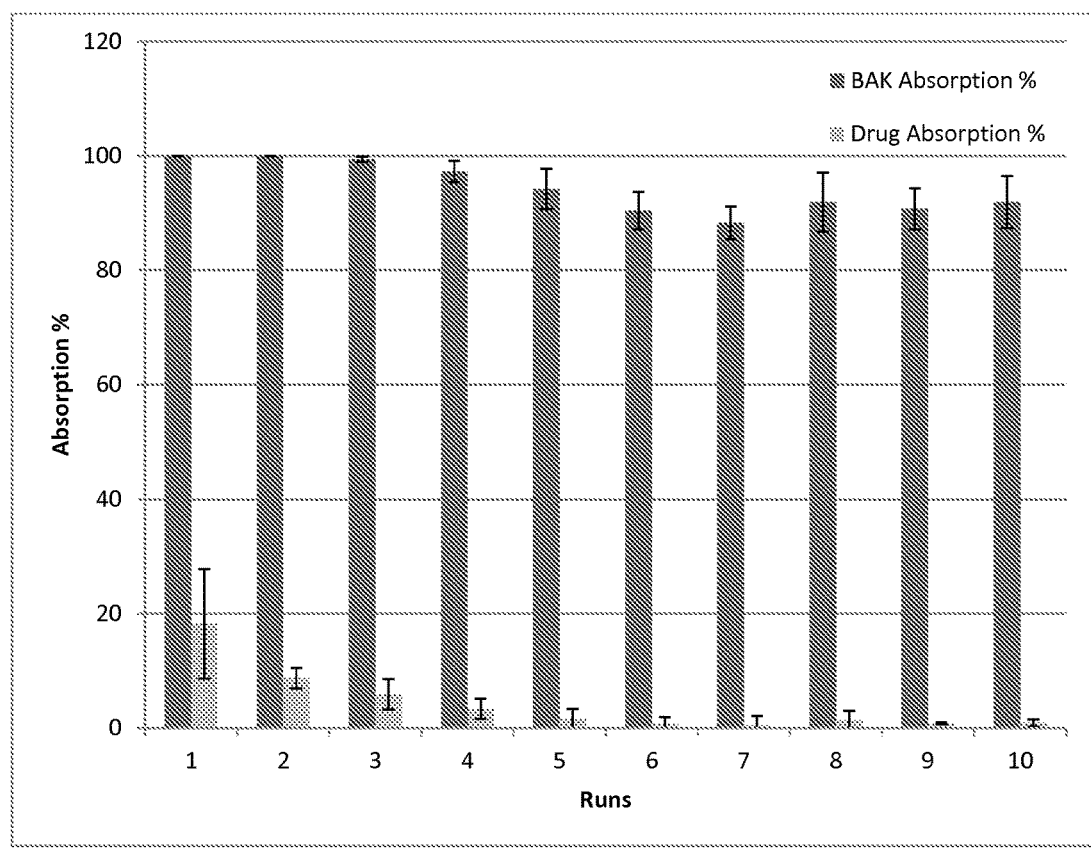
FIG. 26 shows a bar chart of the percentages of BAK and timolol that are removed after passing 1.5 mL of a timolol/

FIGS. 26 and 27 showed the percentages of BAK and timolol that absorbed in the filter from the mixture after each aliquot was passed through the pHEMA particles prepared by using SR454HP and SR9035 as cross-linker, respectively. In FIG. 26, nearly 100% of the BAK was removed by the particles in the first 3-5$^{th}$ runs, but reduced to about 90% after the 5$^{th}$ run. About 18% of timolol was removed in the 1$^{st}$ run while the amount removed became negligible in the 10$^{th}$ run. In FIG. 27, pHEMA particles prepared by using SR9035 as cross-linker showed a slightly better BAK removal capacity, where nearly 100% of the BAK was removed by the particles in the first 6$^{th}$ runs, but reduced to about 95% in the 10$^{th}$ run. About 25% of timolol was removed in the 1$^{st}$ run while the amount removed became negligible after the 5$^{th}$ run.

Pre-Loading the Filter with BAK or an Alternative Preservative

Based on the US Code of Federal Regulations, Title 21, Volume 4 (21CFR200.50), section 200.50 on ophthalmic preparations and dispensers, "all preparations offered or intended for ophthalmic use, including preparations for cleansing the eyes, should be sterile. It is further evident that such preparations purport to be of such purity and quality as to be suitable for safe use in the eye"

As the applied pressure on the eye drop bottle is removed after instilling an eye drop, the remaining liquid at the tip is drawn back into the bottle. This liquid drop could carry bacteria with it. In a normal eye drop bottle, the bacteria would enter the solution where the BAK would keep the solution preserved, preventing bacterial growth. In the bottle with the plug, the bacteria may get trapped in the plug where it could potentially grow. To avoid this possibility, the plug must be a sterile environment. To achieve a sterile environment, BAK was incorporated into the plug by soaking the material comprising the plug into BAK solutions prior to assembling the plug or by eluting a certain volume of the BAK solution through the plug after assembly. Although BAK is a preservative, surprisingly a pHEMA plug loaded with BAK provides a sterile environment even though the BAK is adsorbed into the polymer matrix and not in the void space in the plug.

The effect of BAK preloading in the pHEMA particles was examined to determine the maintenance of sterility. BAK was preloaded into pHEMA particles prepared by heat-initiated polymerization, and the plug of these particles integrated in the eye drop prototype was filled with about $10^7$ cfu/mL Escherichia coli (E. coli, a strain of XL1-Blue obtained from Stratagene, Santa Clara, Calif.) in PBS. The plug was incubated at 37° C. for 24 hours to see if E. coli survived, flourished, or diminished under the BAK preloaded environment. Preloading the particles with BAK was carried out by soaking about 80 mg of pHEMA particles in 166 µg/mL of BAK/PBS solution for 7 days. Based on the partition coefficient of BAK in pHEMA particles prepared by heat-initiated polymerization being about 200-250, and the density of the particles being about 1.2 g/mL, the particles load to about 1 mg of BAK, i.e., a concentration of about 1.25%, compared to 0.004-0.0025% in most formulations. The high partition coefficient allows significant BAK uptake into the material without any risk of toxicity from elution of BAK into the eyes. Alternately, this concentration is achieved by passing 8 mL (half a typical eye drop bottle volume) of 0.12 mg/mL of BAK solution through the pHEMA plug. The BAK preloaded particles were then packed in the prototype bottle with a packed length of 8 mm as the device shown in FIG. 19. The eye drop bottle was filled with PBS solution contained with $10^7$ cfu/mL of E. coli. After three drops of the E. coli contained solution were squeezed through the packed particles, the tip including the packed particles was detached from the bottle such that the solution was retained in the plug. The tip was incubated at 37° C. for 24 hours. After 24 hours of incubation, the tip was attached to another clean eye drop bottle contained with fresh PBS solution. Three drops of fresh PBS solution was pushed through the packed particles to wash out the solution residing in the plug. The three drops created before and after incubation were both collected and properly diluted if needed to determine the concentrations of E. coli within the drops. The concentrations were determined by drop plating on agar and counting the colonies on the agar plates. As control, the same experiment procedure was repeated for pure pHEMA particles without preloading BAK.

Table 6, below, summarized the sterile test results. The initial concentration of E. coli in the solution is about $10^7$ cfu/mL. To ensure that E. coli did not get trapped in the filter plug, the concentration of E. coli in the three drops squeezed through the pHEMA plug were measured. The concentration of E. coli after passing through the plug was in the same order as initial concentration, which indicated that the pore size of few microns could not trapped the bacteria. The solution remaining in the plug was incubated for 24 hours and the plug washed with three drops of fresh PBS. The solution washed from the plug was collected and its concentration of E. coli was determined. As shown in Table 6, without preloaded with BAK, the washed solution has a high E. coli concentration of $13.30 \times 10^6$ cfu/mL, although this concentration does not represent the actual concentration of E. coli remaining in the plug. The empty space in the plug was about 20 µL, but one single drop of fresh PBS is about 30 µL, such that the 3 drops of fresh PBS leads to a significant dilution and the actual concentration of the solution remaining in the plug could be 4 to 5 times higher. This result indicates that pHEMA particles that are not preloaded with BAK, allows growth of microorganism in the plug. On the other hand, if the particles were preloaded with sufficient BAK, most of the E. coli does not survive in the filter plug, and the concentration became undetectable. US Federal Regulations require that ophthalmic preservatives achieve 1.0 and 3.0 log reduction by days 7 and 14, respectively, along with no increase in survivors from days 14-28 and no increase in survivors for the fungi from day 0 to day 28 after inoculation with $10^6$ colony forming units (cfu)/mL. The plug loaded with BAK performed significantly better than the regulatory requirements suggesting that the sterility could be achieved at a lower starting concentration of BAK in the plug. With each instillation of eye drop, the concentration of BAK in the plug increases which will improve the degree of sterility.

In an alternate embodiment of the invention, one can load the filter plug with an additional preservative. The second preservative will be chosen to be: ocularly compatible; of a larger molecular weight than BAK; and have a lower affinity for the filter material compared to BAK. When the filter is loaded with this preservative, the larger molecular weight will prevent it from diffusing out during the eye drop instillation. However it will slowly diffuse out possibly in very small quantities into the liquid remaining in the filter after the eye drop is instilled to render it sterile. The small amount of the preservative that diffuses out will eventually be instilled into the eye in the next cycle of eye drop administration but this amount can be minimized by minimizing the volume of the tip filter. The volume for the filter is 10-300 microliter.

The sterile plug can be used for other purposes in addition to preservative removal. It could for example be useful for minimizing oxygen entry into the container when including oxygen scavenging materials. This can protect easily oxidizable formulations. The oxygen scavenging material can be integrated into the plug by incorporating particles that scavenge oxygen along with the sterile particles comprising the plug or the oxygen scavenger can be a separate layer above or below the sterility imparting and/or BAK sequestering material. Oxygen scavenging materials can include iron or ferrous carbonate combined with sodium chloride or other metal halide, ascorbate, sodium hydrogen carbonate, or other scavengers, which can be within the plug material or included in another polymeric matrix. The sterile plug can be used to maintain sterility of the formulation without including any preservative in the formulation. Any contaminates that enter through the plug get trapped in the pores of the plug and get killed by the preservative loaded in the plug. To further ensure that the microorganisms that enter the plug are retained, the plug can be designed to prevent drainage of the fluid back into the container by including values or alternatively by choosing the pore size such that the Young Laplace pressure across the meniscus supports the vacuum in the container, essentially creating a surface-tension seal. Alternatively, rough particles could pin the contact line, trapping liquid in the plug. Employing materials with a variety of pore sizes can permit liquid drainage that occurs quickly from the largest pore to create an air channels that will equalize the pressure, preventing any further drainage. As an example, a plug packed with particles shown in FIG. 25 remains fully filled with water even after the pressure on the eye drop bottle has been released. Retaining the fluid in the plug in the interim between successive instillations can sequester preservatives or other components that adsorb slowly on the polymer. When the plug remains filled with fluid at all times, drops squeezed from the device have contacted the plug material for periods of a few hours to a day, compared to a few seconds when the plug dried in the interim period because of drainage back to the container.

TABLE 6

Concentration of E. coli as determined by colony count

| Plug material | Initial concentration before passing through the plug ($10^6$ cfu/mL) | Concentration after passing through the plug ($10^6$ cfu/mL) | Concentration in the plug after incubation for 24 hours ($10^6$ cfu/mL) |
|---|---|---|---|
| Pure pHEMA particles | 9.83 | 9.93 | 13.30 |
| pHEMA particles preloaded with BAK$^a$ | 9.83 | 15.40 | 0 |

$^a$The BAK loading concentration in particles is about 12.35 µg/mg = 1.23% (w/w) compared to 0.004-0.025% in the formulations.

Incorporation of One-Way Valves in the Bottle.

If a bottle has the plug contacting the liquid, there will be a slow uptake of preservative. Typically, months are required for the BAK to absorb into the filter because of long diffusion lengths. A valve can also be placed in the bottle immediately preceding the filter plug to allow flow only when a critical pressure is exceeded. A valve may be incorporated in the side of the bottle to allow air to be included when the pressure for drop dispensing is removed. This valve allows pressure equilibration through flow in of air rather than draining back of the fluid.

BAK Dilution in the Bottle

As the applied pressure on the eye drop bottle is removed after instilling an eye drop, the remaining liquid in the plug can be sucked back in due to the vacuum created in the bottle. This liquid is devoid of BAK and so its drainage back into the bottle will dilute the BAK concentration. This effect becomes particularly significant towards the end when only a few drops are left in the bottle. This dilution effect can be minimized by using plugs with very small void volume. Plugs with volumes less than three times of that of the eye drops and most preferably less than one eye drop are advantageous. To avoid BAK free solution from draining back into the bottle, either using a valve or by creating hydrophobic channels in the plug so that water cannot be drawn through but air can, alleviating the driving force for fluid to drain back. The higher the BAK concentration that is used the less one needs to compensate for dilution by solution drawn back into the bottle. Finally, if all these design features are not sufficient to prevent significant dilution, an additional embodiment of the design is to place a preservative loaded membrane in the eye drop bottle so that the membrane can serve as a reservoir to keep the preservative concentration relatively unchanged. The membrane could be made from HEMA and pre-equilibrated with BAK at the same concentration as the formulation in the bottle. The preferred location for the membrane is at the bottom of the container to permit full contact with the formulation, but other shapes could be used, e.g. a large particle added to the formulation. The preferred volume of the film will be about 1-5% of the starting volume of the eye drop formulation. Based on a partition coefficient of 300, a 1-5% volume fraction will imply that the film contains 3-15 times the amount of BAK in the formulation, thereby proving a strong buffering effect protecting against any possibility of dilution of the preservative.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A preservative removing device, comprising a porous hydrophilic polymeric matrix, wherein the porous hydrophilic polymeric matrix comprises a material with a hydraulic permeability greater than 0.01 Da and fits an outlet of a container for a solution, emulsion, or suspension, wherein the porous hydrophilic polymeric matrix rapidly and selectively removes a preservative from the solution, emulsion, or suspension that flows through the porous hydrophilic polymer matrix with a pressure drop, wherein a time scale for binding the preservative is shorter than a time scale for drop formation and wherein the device is configured to remove at least 50% of the preservative and retain at least 50% of an ophthalmic agent within the solution, emulsion or suspension.

2. The preservative removing device according to claim 1, wherein the porous hydrophilic polymeric matrix has a partition coefficient for the preservative from the solution, emulsion, or suspension of at least 100.

3. The preservative removing device according to claim 1, wherein the porous hydrophilic polymeric matrix comprises particles.

4. The preservative removing device according to claim 1, wherein the porous hydrophilic polymeric matrix is preloaded with the preservative at 1 to 90% of saturation of the preservative in the porous hydrophilic polymeric matrix.

5. The preservative removing device according to claim 1, wherein the porous hydrophilic polymeric matrix comprises poly hydroxyl ethyl methacrylate (pHEMA), poly hydroxyl ethyl methacrylate-co-methacrylic acid, or a combination thereof.

6. The preservative removing device according to claim 1, wherein the porous hydrophilic polymeric matrix has interconnected pores, wherein the pores have an average radius of 1 to 60 µm.

7. The preservative removing device according to claim 1, wherein the porous hydrophilic polymeric matrix is partitioned as microparticles with cross-sections of 2 to 100 µm.

8. The preservative removing device according to claim 1, wherein the hydraulic permeability is greater than 1 Da.

9. The preservative removing device according to claim 1, wherein the preservative is benzalkonium chloride (BAK).

10. The preservative removing device according to claim 9, wherein the porous hydrophilic polymeric matrix is preloaded with the BAK at a concentration of one to 100 times that of the solution, emulsion, or suspension in the container.

11. The preservative removing device according to claim 9, wherein the porous hydrophilic polymeric matrix is preloaded with a second preservative.

12. The preservative removing device according to claim 1, wherein the porous hydrophilic polymeric matrix includes a hydrophilic drug at a level below saturation.

13. The preservative removing device according to claim 1, further comprising antibacterial microparticles.

14. The preservative removing device according to claim 13, wherein the antibacterial microparticles comprise silver.

15. The preservative removing device according to claim 9, further comprising an oxygen scavenger.

16. A multi-dosing device for delivery of an ophthalmic solution, comprising a compressible bottle; a preservative removing device according to claim 1 comprising a porous hydrophilic polymeric matrix, a solution comprising an ophthalmic agent, a preservative, wherein the bottle comprises an outlet extension, wherein the preservative removing device when dry has dimensions smaller than an internal dimensions of the outlet extension, wherein the preservative removing device when wet has dimensions larger than the internal dimensions of the outlet extension.

17. The multi-dosing device according to claim 16, further comprising a preservative source, preservative source comprising a pHEMA membrane included at 1-10% by volume of the solution volume, wherein the pHEMA membrane includes the preservative at a concentration equal to the solution.

18. The multi-dosing device according to claim 16, wherein the porous hydrophilic polymeric matrix comprises poly hydroxyl ethyl methacrylate (pHEMA).

19. The multi-dosing device according to claim 16, wherein the preservative is benzalkonium chloride (BAK).

20. The multi-dosing device according to claim 16, wherein the ophthalmic agent comprises timolol, dorzolamide, dexamethasone phosphate, dexamethasone, or latanoprost.

21. The preservative removing device according to claim 1, wherein the preservative removing device is capable of forming a drop of the solution, emulsion, or suspension in about 3 seconds with the pressure drop, the pressure drop comprising a pressure drop formed with compressed air from an elastic eyedropper bottle.

* * * * *